(12) United States Patent
Odawara et al.

(10) Patent No.: US 9,881,711 B2
(45) Date of Patent: Jan. 30, 2018

(54) BEAM TRANSPORT SYSTEM AND PARTICLE BEAM THERAPY SYSTEM

(71) Applicant: Mitsubishi Electric Corporation, Chiyoda-ku, Tokyo (JP)

(72) Inventors: Shuhei Odawara, Tokyo (JP); Kazushi Hanakawa, Tokyo (JP)

(73) Assignee: MITSUBISHI ELECTRIC CORPORATION, Chiyoda-Ku, Tokyo (JP)

( * ) Notice: Subject to any disclaimer, the term of this patent is extended or adjusted under 35 U.S.C. 154(b) by 0 days.

(21) Appl. No.: 15/313,499

(22) PCT Filed: Sep. 12, 2014

(86) PCT No.: PCT/JP2014/074204
§ 371 (c)(1),
(2) Date: Nov. 22, 2016

(87) PCT Pub. No.: WO2016/038731
PCT Pub. Date: Mar. 17, 2016

(65) Prior Publication Data
US 2017/0213613 A1 Jul. 27, 2017

(51) Int. Cl.
*A61N 5/00* (2006.01)
*G21K 1/093* (2006.01)
(Continued)

(52) U.S. Cl.
CPC .......... *G21K 1/093* (2013.01); *A61N 5/1081* (2013.01); *G21K 1/087* (2013.01); *G21K 1/10* (2013.01);
(Continued)

(58) Field of Classification Search
None
See application file for complete search history.

(56) References Cited

U.S. PATENT DOCUMENTS 5,986,274 A * 11/1999 Akiyama ................. A61N 5/10
250/492.1
6,218,675 B1 * 4/2001 Akiyama ............. A61N 5/1043
250/396 ML
(Continued)

FOREIGN PATENT DOCUMENTS

JP 2003-282300 A 10/2003
JP 4536826 B1 9/2010
(Continued)

OTHER PUBLICATIONS

International Search Report (PCT/ISA/210) dated Nov. 18, 2014, by the Japanese Patent Office as the International Searching Authority for International Application No. PCT/JP2014/074204.
(Continued)

*Primary Examiner* — Andrew Smyth
(74) *Attorney, Agent, or Firm* — Buchanan Ingersoll & Rooney PC

(57) ABSTRACT

A beam shaping device included in a beam transport system is provided with: a pre-stage quadrupole electromagnet that reduces a distribution width of x-angle components that are inclinations in the x-direction of the charged particles in the beam with respect to the traveling direction; a penumbra expander that moderates an end profile of a particle-number distribution of the x-angle components in the beam having passed through the pre-stage quadrupole electromagnet; and a post-stage quadrupole electromagnet that adjusts a betatron phase in a phase-space distribution in the x-direction, of the beam having passed through the penumbra expander; wherein the post-stage quadrupole electromagnet adjusts a phase advance angle of the betatron phase from the penumbra expander to the isocenter, to be in a range of an odd multiple of 90 degrees±45 degrees.

20 Claims, 17 Drawing Sheets

(51) Int. Cl.
*A61N 5/10* (2006.01)
*G21K 1/10* (2006.01)
*H05H 13/04* (2006.01)
*H05H 7/00* (2006.01)
*G21K 1/087* (2006.01)
*G21K 5/04* (2006.01)

(52) U.S. Cl.
CPC ............... *G21K 5/04* (2013.01); *H05H 7/001* (2013.01); *H05H 13/04* (2013.01); *H05H 2007/002* (2013.01); *H05H 2007/005* (2013.01)

(56) References Cited

U.S. PATENT DOCUMENTS

| | | |
|---|---|---|
| 2004/0232356 A1 | 11/2004 | Norimine et al. |
| 2011/0108737 A1 | 5/2011 | Pu et al. |
| 2014/0110596 A1 | 4/2014 | Chang |
| 2015/0038764 A1 | 2/2015 | Sugahara et al. |

FOREIGN PATENT DOCUMENTS

| | | |
|---|---|---|
| JP | 4639401 B2 | 2/2011 |
| JP | 2011-050660 A | 3/2011 |
| TW | 201347803 A | 12/2013 |
| TW | 201421529 A | 6/2014 |

OTHER PUBLICATIONS

Written Opinion (PCT/ISA/237) dated Nov. 18, 2014, by the Japanese Patent Office as the International Searthing Authority for International Application No. PCT/JP2014/074204.

* cited by examiner $\Delta \phi = 90*(2n-1)$

BEAM TRANSPORT SYSTEM AND PARTICLE BEAM THERAPY SYSTEM

TECHNICAL FIELD

The present invention relates to a beam transport system for transporting a charged particle beam formed of charged particles such as protons, heavy particles or the like, and a particle beam therapy system in which the transported charged particle beam is irradiated to an object to be irradiated, such as a physical body, a human body or the like.

BACKGROUND ART

In general, a particle beam therapy system includes: a beam generation apparatus for generating a charged particle beam; an accelerator connected to the beam generation apparatus, for accelerating the generated charged particle beam; a charged-particle beam transport system for transporting the charged particle beam emitted from the accelerator after being accelerated therein up to a setup given energy; and a particle beam irradiation apparatus placed on the downstream side of the beam transport system, for irradiating the charged particle beam to an irradiation target.

When the beam is extracted using a resonant extraction scheme from a synchrotron as the accelerator, or when the beam is extracted from a cyclotron as the accelerator and a collimator is being provided in the beam transport system, the particle distribution in cross-sectional direction of the beam results in a profile in which the number of charged particles decreases drastically at the ends, like a rectangular shape, for example. In the case where an irradiation field is formed by scanning the beam like in the spot-scanning irradiation method or the raster-scanning irradiation method, when the number of charged particles decreases drastically at the ends of the dose distribution as shown in FIG. 2 and FIG. 3, a following problem arises. FIG. 2 and FIG. 3 are diagrams each illustrating positional displacement and robustness of a beam. FIG. 2 corresponds to a case where the ends of the particle-beam distribution are moderate, and FIG. 3 corresponds to a case where the ends of the particle-beam distribution vary steeply. In FIG. 2 and FIG. 3, the abscissa represents a beam scanning direction X in the irradiation target, and the ordinate represents a dose (charged-particle number). Dose distributions 81, 86 each indicated by a broken line, are each a dose distribution at one irradiation position in the spot-scanning irradiation method. Dose distributions 87, 88 in FIG. 3 correspond to a case where the beam profile and the beam irradiation position are as planned and thus there is no displacement in the beam-irradiation position. Dose distributions 89, 90 in FIG. 3 correspond to a case where the beam profile and the beam irradiation position are not as planned and a displacement occurs in the beam-irradiation position. The respective dose distributions 87, 89 in FIG. 3 are each a dose distribution at each of the irradiation positions, and the dose distributions 88, 90 in FIG. 3 are each an integrated dose distribution in the overall irradiation field. As shown in FIG. 3, in the case where the beam having a dose distribution whose ends vary steeply is irradiated, the flatness of the dose distribution 90 in the formed irradiation, field is largely deteriorated in response to a displacement in the beam profile or in the beam-irradiation position.

In contrast, as shown in FIG. 2, in the case of the distribution, like a Gaussian distribution, in which the charged-particle number variation at the ends is moderate, it is possible to make the flatness of the dose distribution 85 in the irradiation field better than, that in FIG. 3. Like in FIG. 3, dose distributions 82, 83 in FIG. 2 correspond to a case where the beam profile and the beam irradiation position are as planned and thus there is no displacement in the beam-irradiation position. Like in FIG. 3, dose distributions 84, 85 in FIG. 2 correspond to a case where the beam profile and the beam irradiation position are not as planned and a displacement occurs in the beam-irradiation position. The respective dose distributions 82, 84 in FIG. 2 are each a dose distribution at each of the irradiation positions, and the dose distributions 83, 85 in FIG. 2 are each an integrated dose distribution in the overall, irradiation field. As shown in FIG. 2, in the case where the beam having the distribution, like a Gaussian distribution, in which the charged-particle number variation at the ends is moderate, is irradiated, the flatness of the dose distribution 85 in the formed irradiation field is improved against the displacement in the beam profile or in the beam-irradiation position, in comparison with the dose distribution 90 in FIG. 3.

In the case of forming an irradiation field by scanning the beam, when the charged-particle number decreases drastically at the ends of the dose distribution, the robustness against a change in the irradiation position or beam profile, or a displacement in the irradiation position is impaired, so that it becomes difficult to form the irradiation field that is flat in the dose distribution. For example, when the charged-particle number decreases drastically at the ends of the dose distribution, it is necessary to control the irradiation position and the size of the beam, for example, up to 0.1 mm or less.

In Patent Document 1, a charged particle irradiation system, is described that modifies the charged particle distribution, which corresponds to a case where the charged-particle number decreases drastically at the ends of the dose distribution and in which the emittance ellipses in an X-direction and a Y-direction are asymmetric to each other, into a Gaussian distribution both in the X-direction and the Y-direction. The charged particle irradiation, system of Patent Document 1 includes, in its beam transport system extending from the accelerator to an irradiation section, an up-stream-side electromagnet comprising four quadrupole electromagnets, a scatterer provided downstream of the electromagnet, and a downstream-side electromagnet provided downstream of the scatterer and comprising four quadrupole electromagnets. In the charged particle irradiation system of Patent Document 1, the beam whose emittance ellipses in the X, Y-directions are asymmetric to each other is modified by the upstream-side electromagnet so that position components X and Y in the emittance ellipses are the same, and then the angle components in the Y-direction are expanded by multiple, scattering using the scatterer to thereby make same the emittances in the X, Y directions. Thereafter, the beam is adjusted to have an intended beam diameter by adjusting the emittances in the X, Y-directions using the downstream-side electromagnet.

CITATION LIST

Patent Document

Patent Document 1: Japanese Patent No. 4639401 (Paragraph [0020], Paragraph [0044] to Paragraph [0046], FIG. 1, FIG. 7)

SUMMARY OF THE INVENTION

Problems to be Solved by the Invention

According to Patent Document 1, when, in order to achieve the distribution in which the particle number varies moderately at the ends like in a Gaussian distribution, the distribution profile is modified, using the scatterer as shown in Patent Document 1, the real-space profile of the beam that is going to enter the scatterer for modifying the distribution, is modified so that the smaller beam size in a y-direction and the larger beam size in an x-direction are made the same. However, because the real-space profile of the entering beam was hot optimized, it is necessary to use the scatterer having a large scattering angle in order to largely expand the angle components x' in the x-direction in which the emittance is smaller. According to Patent Document 1, because the emittance is largely expanded, it is difficult to irradiate such a beam whose size is small, for example, 5 mm or less that is required for highly-accurate scanning irradiation, and in which the charged-particle number variation at the ends of the distribution is moderate. Furthermore, according to Patent Document 1, because the expansion in the emittance is very large, an increase in the beam size will also be very large during transportation of the beam in the section from the scatterer to the irradiation position. In order to avoid that increase, the scatterer is difficult to be placed at a position away from the irradiation position. If the scatterer is placed near the irradiation position, there arises a problem of an unwanted exposure due to neutrons produced from the scatterer and an increase in the size of the system for ensuring the device installation space.

Further, according to the method, of Patent Document 1, in the case where the charged-particle number variation is steep at the ends only in one direction along the beam cross-sectional direction and the distribution profile at the irradiation position is to be optimized using a normal isotropic scatterer so that the particle number variation at the ends is moderate, because it is necessary to make negligible the influence on a distribution profile in the angular direction after passing through the scatterer, by the distribution profile before passing through the scatterer, the scatterer having a very large scattering angle is required to be used, so that a distribution in a direction that is unnecessary to be modified is also expanded largely.

This invention has been made to solve the problems as described above, and a first object thereof is to provide a beam transport system which includes a beam shaping device for shaping a charged particle beam, without undesirably increasing its beam size, into the beam having a distribution in which the particle-number varies moderately at its ends. Further, a second, object thereof is to provide a beam transport system which includes a beam shaping device that can be placed at a position away from the irradiation position.

Means for Solving the Problems

The beam transport system according to the invention is a beam transport system which comprises a bears shaping device by which a distribution profile of a charged particle beam having, at an end in a cross-sectional direction of the beam, a steep portion where a particle number varies steeply, is shaped into a moderated form; and which transports the charged particle beam to an irradiation target that is positioned so as to include an isocenter as a positional reference for irradiation. Assuming that a direction perpendicular to a traveling direction of the charged particle beam and passing from a center of the charged particle beam to the steep portion is an x-direction, and inclinations of charged particles forming the charged particle beam with respect to the traveling direction, are angle components, the beam shaping device in the beam transport system is characterized by comprising: a pre-stage quadripole electromagnet that reduces a distribution width of x-angle components that are the angle components in the x-direction in the charged particle beam; a penumbra expander that moderates an end profile of a particle-number distribution of the x-angle components in the charged particle beam, having passed through the pre-stage quadrupole electromagnet; and a post-stage quadrupole electromagnet that adjusts a betatron phase in a phase-space distribution in the x-direction, of the charged particle beam having passed through the penumbra expander; wherein the post-stage quadrupole electromagnet adjusts the betatron phase so that a phase advance angle thereof from the penumbra expander to the isocenter is in a range of an odd multiple of 90 degrees±45 degrees.

Effect of the Invention

In the beam transport system according to the invention, after the distribution width of the angle components in the x-direction of the charged particle beam to be inputted to the penumbra expander is reduced, the end profile is moderated by the penumbra expander and then, the phase advance angle of the betatron phase toward the isocenter is adjusted. Thus, it is possible to transport a charged particle beam having a distribution in which the particle-number varies moderately at its end, without undesirably increasing the beam size.

MODES FOR CARRYING OUT THE INVENTION

Embodiment 1

Figure 1:
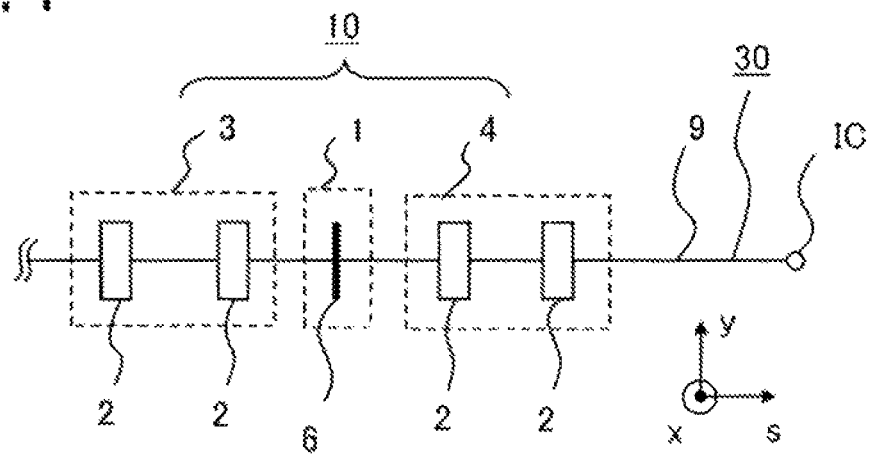
FIG. 1 is a diagram showing a beam transport system according to Embodiment 1 of the invention.
Figure 2:
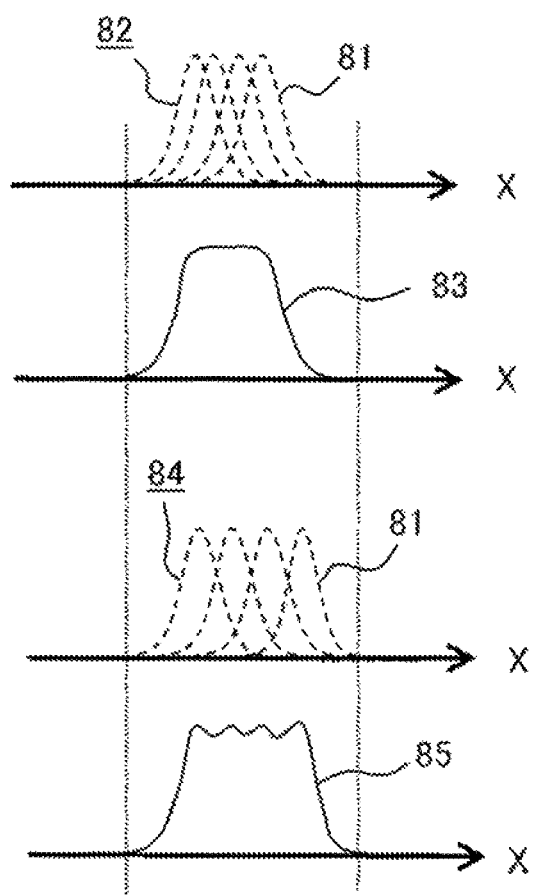
FIG. 2 is a diagram illustrating positional displacement and robustness of a beam.
Figure 3:
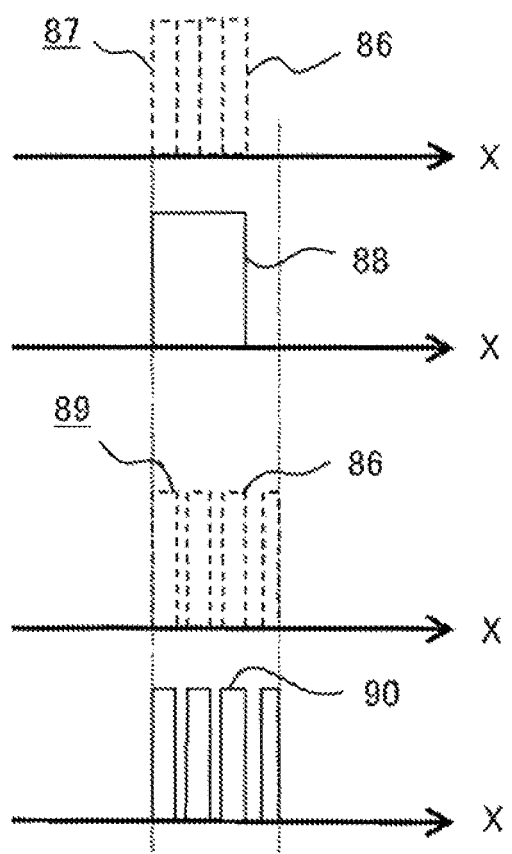
FIG. 3 is a diagram illustrating positional displacement and robustness of a beam.
Figure 4:
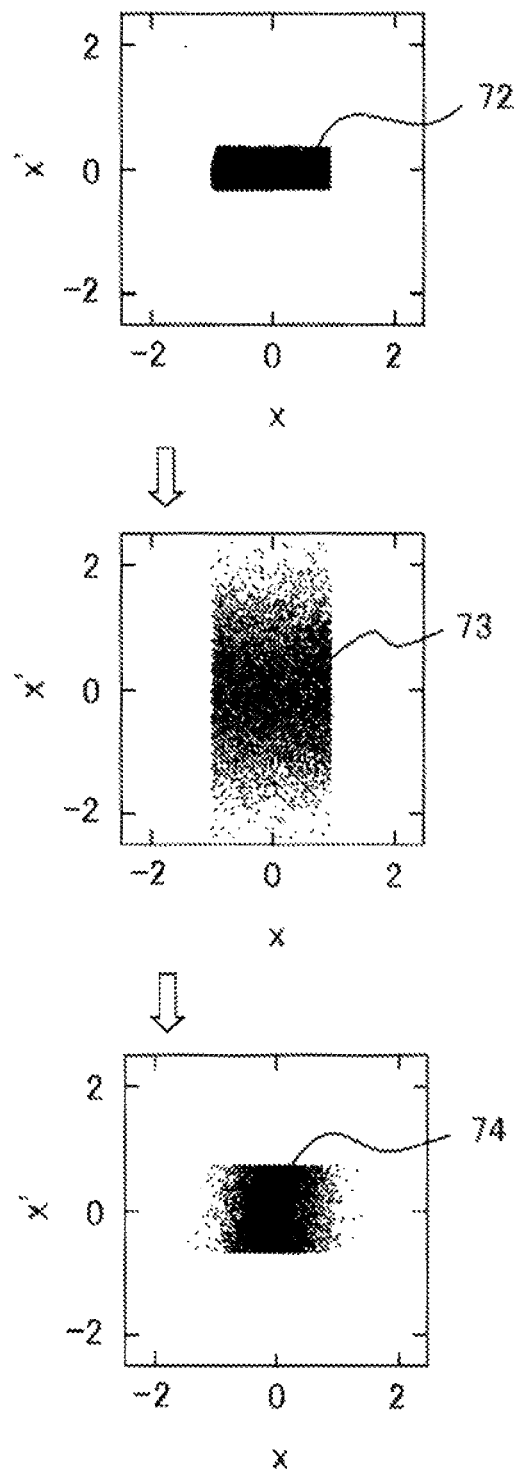
FIG. 4 is a diagram illustrating concept of beam transportation in the beam transport system of FIG. 1.
Figure 5:
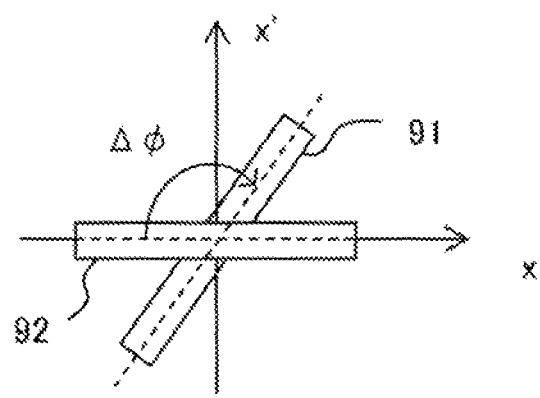
FIG. 5 is a diagram illustrating a change in betatron phase caused by a post-stage quadrupole electromagnet shown in FIG. 1.
Figure 6:
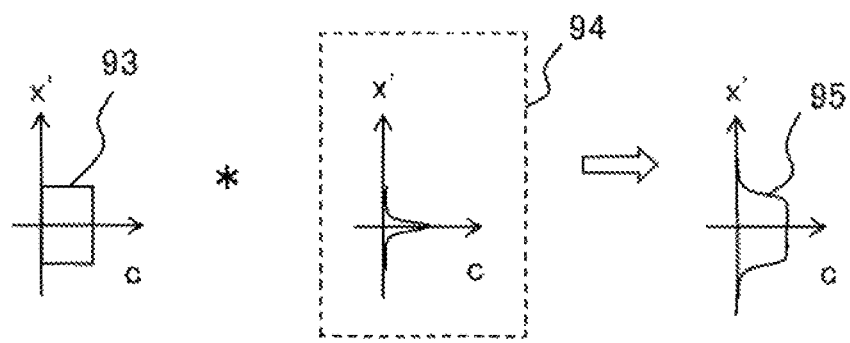
FIG. 6 is a diagram illustrating a change in phase-space distribution before and after passing through a penumbra expander.
Figure 7:
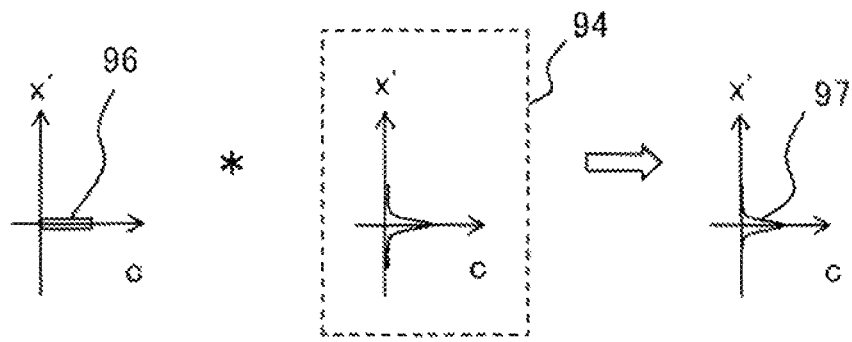
FIG. 7 is a diagram illustrating a change in phase-space distribution before and after passing through a penumbra expander.

Here, such a case is assumed in which, with respect to the particle distribution in a beam cross-sectional direction (a direction perpendicular to the beam traveling direction), its ends in one direction (x-direction) each have a profile in which the charged-particle number decreases drastically, like in a rectangular shape, for example, and its ends in the other direction (y-direction) each have a profile in which the charged-particle number decreases moderately. At the end in the beam cross-sectional direction, a portion where the particle number varies steeply is a steep portion. FIG. 1 is a diagram showing a beam transport system according to Embodiment 1 of the invention. FIG. 4 is a diagram illustrating concept of beam transportation in the beam transport system in FIG. 1, and FIG. 5 is a diagram illustrating a change in betatron phase caused by a post-stage quadrupole electromagnet shown in FIG. 1. FIG. 6 and FIG. 7 are diagrams each illustrating a change in phase-space distribution before and after passing through a penumbra expander. A beam transport system 30 that transports a charged particle beam generated and accelerated in a beam generation apparatus to a particle beam irradiation apparatus, includes a beam shaping device 10. The beam shaping device 10 includes: a penumbra expander 1 that moderates an end profile of a dose distribution in one-shot of the charged particle beam; a pre-stage quadrupole electromagnet 3 placed, on the upstream side of the penumbra expander 1; and a post-stage quadrupole electromagnet 4 placed on the downstream side of the penumbra expander 1. The charged particle beam, is brought along a beam passage 9 of the beam transport system to an isocenter IC as a positional reference for beam irradiation. The beam transport system 30 transports the charged particle beam to an irradiation target that is positioned so as to include the isocenter IC. A penumbra corresponds to a width extending from 20% to 80% of the maximum value in the dose distribution (particle-number distribution) of the charged particle beam such as the dose distribution 81 shown in FIG. 2, and the larger the value of the penumbra is, the more moderate the end profile of the dose distribution becomes. The penumbra expander 1 expands a penumbra with a very small value meaning that the end profile of the dose distribution is steep, into a penumbra with a large value.

The pre-stage quadrupole electromagnet 3 includes at least two quadrupole electromagnets 2, and the post-stage quadrupole electromagnet 4 includes at least two quadrupole electromagnets 2. The penumbra expander 1 is, for example, a scatterer 6. As the scatterer 6, an aluminum member whose thickness is about 0.01 mm to 0.1 mm is used. The pre-stage quadrupole electromagnet 3 is provided for making narrow the distribution of the angle components in a direction in which the end profile of the dose distribution in one-shot of the charged particle beam, namely, the particle-number variation at the ends in one-shot of the charged particle beam, is desired to he moderated. The post-stage quadrupole electromagnet 4 is provided for adjusting the advancement in the betatron phase between the scatterer 6 and the isocenter IC as the beam irradiation position placed downstream of the scatterer 6, for example, for adjusting the advancement to be an odd multiple of 90 degrees. The angle component is an inclination in the phase-space distribution with respect to the beam traveling direction s. Namely, the angle component in the x-direction is x'(dx/ds), and the angle component in the y-direction is y'(dy/ds). The x-direction and the y-direction are perpendicular to the beam traveling direction s, and the x-direction and the y-direction are perpendicular to each other.

The concept of beam transportation using the beam shaping device 10 will be described using FIG. 4. The description will be made assuming that the direction in which the particle-number variation at the ends in one-shot of the charged particle beam is desired to be moderated, is x. A phase-space distribution 72 in FIG. 4 is a phase-space distribution shaped by the pre-stage quadrupole electromagnet 3, namely, a phase-space distribution at the inlet side of the scatterer 6. A phase-space distribution 73 in FIG. 4 is a phase-space distribution shaped by the scatterer 6, namely, a phase-space distribution at the outlet side of the scatterer 6. A phase-space distribution 74 in FIG. 4 is a phase-space distribution adjusted in its betatron phase by the post-stage quadrupole electromagnet 4, namely, a phase-space distribution at the isocenter IC. In the three phase-space distributions in FIG. 4, a real-space component x and an angle component x' are both normalized, so that they are represented as values relative to their respective given values. The real-space component x and the angle component x', will be simply referred to as x-component and x'-component, if appropriate. Using the pre-stage quadrupole electromagnet 3, the distribution of the angle components x' in the direction in which the end profile of the dose distribution in one-shot of the charged particle beam is desired to be moderated, is narrowed so that a distribution width, that is the breadth of the distribution, becomes as small as possible, as shown in the phase-space distribution 72. It is desired that the distribution width of the angle components x' be made extremely small at the position of the scatterer 6 by changing the parameters of the quadrupole electromagnets 2.

Using the scatterer 6 as the penumbra expander 1, the distribution of the angle components x' is expanded as shown in the phase-space distribution 73. Using the post-stage quadrupole electromagnet 4 placed downstream of the scatterer 6, the betatron phase is controlled so that a distribution of the angle components x' in which the variation has been moderated by the scatterer 6, is reflected in a distribution in the real-space direction x of the phase-space distribution at the isocenter IC. FIG. 5 is a diagram illustrating a change in the betatron phase caused by the post-stage quadrupole electromagnet shown in FIG. 1. A phase-space distribution 92 is an example of the phase-space distribution at the upstream side (inlet side) of the post-stage quadrupole electromagnet 4, and a phase-space distribution 91 is an example of the phase-space distribution at the downstream side (outlet side) of the post-stage quadrupole electromagnet 4. The betatron phase of the phase-space distribution 91 is advanced by Δφ from that of the phase-space distribution 92.

By the quadrupole electromagnets 2 of the post-stage quadrupole electromagnet 4, the betatron phase is adjusted and the beam width that corresponds to the real-space components in the x-direction in the phase-space distribution is shaped into a specified size. As described above, according to the beam transport system that includes the beam shaping device 10, because of the beam shaping device 10, a beam having a real-space distribution in which the particle-number variation at the ends is moderate can be supplied to the irradiation position (isocenter IC). Note that the phase-space distribution 74 in FIG. 4 is an example resulted from the phase-space distribution 73 after its betatron phase is advanced by an odd multiple of 90 degrees, When the advancement in the betatron phase is 0 degree or 180 degrees, the particle-number variation at the ends in the real-space distribution remains steep, and as the advance angle of the betatron phase becomes closer to 90 degrees or 270 degrees, the particle-number variation at the ends in the real-space distribution becomes more moderate. When the advance angle of the betatron phase is 90 degrees or 270 degrees, it is possible to make the real-space distribution have a profile in which the right and left penumbras are nearly equal to each other and no flat portion is formed around the center, namely, to make the real-space distribution close to the profile of a Gaussian distribution. That is, when the betatron phase is advanced by an odd multiple of 90 degrees, it is possible to make the real-space distribution have a profile in which the right and left penumbras are nearly equal to each other and no flat portion is formed around the center, namely, to make the real-space distribution close to the profile of a Gaussian distribution. Assuming that a base angle is 90 degrees, it is best that the advance angle of the betatron phase be an odd multiple of the base angle; however, the advance angle may be in a range of an odd multiple of 90 degrees (base angle) ±45 degrees.

The reason why the angle components x' in the phase-space distribution are made extremely narrow before being inputted to the scatterer 6, will be explained. FIG. 6 and FIG. 7 are diagrams each illustrating a change in the phase-space distribution before and after passing through the penumbra expander. FIG. 6 corresponds to a case where the beam having wide angle components x' is inputted to the scatterer 6, and FIG. 7 corresponds to a case where the beam having narrow angle components x' is inputted to the scatterer 6. Angular directional characteristics 93, 96 are each an angular directional characteristic of the beam to be inputted to the scatterer 6, where the ordinate represents the angle component x' and line abscissa represents the charged-particle number c of the beam. An angle-component modification effect 94 is given to show how the scatterer 6 functions to moderate the angle components x', where the ordinate represents the angle component x' and the abscissa represents the charged-particle number c of the beam. Angular directional characteristics 95, 97 are each an angular directional characteristic of the beam having passed through the scatterer 6, where the ordinate represents the angle component x' and the abscissa represents the charged particle number c of the beam. In FIG. 6, it is shown that the Gaussian distribution in the angle-component modification effect 94 is convolved into the rectangular distribution of the angular directional characteristic 93, which results in the angular directional characteristic 95 that is a distribution having penumbras. In FIG. 7, it is shown that the Gaussian distribution in the angle-component modification effect 94 is convolved into the rectangular distribution of the angular directional characteristic 96, which results in the angular directional characteristic 97 that is a distribution having penumbras. Note that, in FIGS. 6 and 7, "*" is used for indicating the convolution as described above.

When the scatterer 6 is thin, in the range of about 0.01 mm to 0.1 mm, the distribution after passing through the scatterer 6, namely, the distribution after scattering, results in a distribution in which the angle-component modification effect 94 by the scatterer 6, is convolved. As shown, in FIG. 7, when the breadth of the angle components x' before scattering is substantially smaller than that of the angle-component modification effect 94 by the scatterer 6, the breadth by the angle-component modification effect 94 becomes dominant in the distribution profile of the angle components x' after scattering. In contrast, as shown in FIG. 6, when the breadth of the angle components x' before scattering is substantially larger than that of the angle-component modification effect 94, portions around the maximum value and the minimum value of the angle components x' become moderate, so that the degree of change in the distribution profile of the angle components x' before and after scattering is smaller than that in FIG. 7. According to the invention, as shown in the phase-space distribution 72 in FIG. 4, the breadth of the angle components x' before scattering is made smaller than that of the angle-component modification effect 94 by the scatterer 6, so that the change in the distribution of the angle components x' by the scatterer 6 can be largest. Because the angle components x' of the beam to be inputted to the scatterer 6 are extremely narrowed, a penumbra expanding effect is sufficiently achieved by the scatterer 6 even if it is poor in modification effect on the angular direction distribution. Namely, it is possible to make the thickness of the scatterer 6 thin while achieving a sufficient penumbra expanding effect. Because the thickness of the scatterer 6 is thin, a change in the beam energy (energy reduction) by the scatterer 6 can be made minimum.

In the case of Patent Document 1, the phase-space distribution is modified so that, just before the scatterer, the beam sizes in the respective real-space directions of x-direction and y-direction are matched to each other and, in addition, a sufficiently large scattering effect is imparted to the distribution profile in the angular direction before scattering, so that the distribution profile after scattering is prevented from being influenced by the distribution profile before scattering and thus the directional dependency between the distribution profiles is negated. Namely, in the case of Patent Document 1, the scatterer is required to have a large scattering effect and thus, its area becomes large and its thickness becomes thick, which results in large energy reduction by the scatterer. Unlike in the case of Patent Document 1, according to the beam shaping device 10 in Embodiment 1 of the invention, because the breadth of the angle components x' before scattering is made smaller than that of the angle-component modification effect 94 by the scatterer 6, it is possible to satisfactorily employ the modification effect on the distribution of the angle components x' by the scatterer 6 even if it is a thin scatterer. Unlike in the case of Patent Document 1, according to the beam shaping device 10 of Embodiment 1 of the invention, because the thickness of the scatterer 6 is thin, a change in the beam energy (energy reduction) by the scatterer 6 can be made minimum.

Description will be made about a direction in which the particle-number variation at the ends in one-shot of the charged particle beam is not required to be moderated, for example, the y-direction. In the y-direction in which the particle-number variation at the ends is not required to be moderated, the particle-number variation at the ends is already moderate. Thus, the processing described above is not applied. However, because the distribution of the angle components y' will also be expanded by the scatterer 6 as the distribution of the angle components x' is expanded by the scatterer 6, there are cases where it is desired to prevent the beam size in the y-direction from increasing. In these cases, the phase distribution is rotated so that the breadth in the angular direction, namely, the angle components y', becomes wider at the position of the scatterer 6. This makes it possible to reduce a change in emittance (area in the phase-space distribution) before and after passing through the scatterer 6, to thereby prevent the beam size from increasing.

Figure 8:
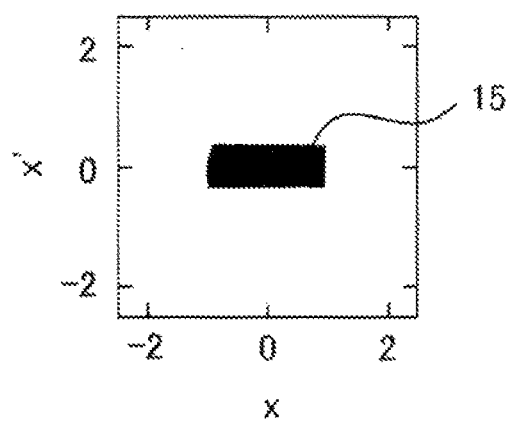
FIG. 8 is a diagram showing a normalized phase-space distribution in an x-direction of the beam to be inputted to the penumbra expander shown in FIG. 1.
Figure 9:
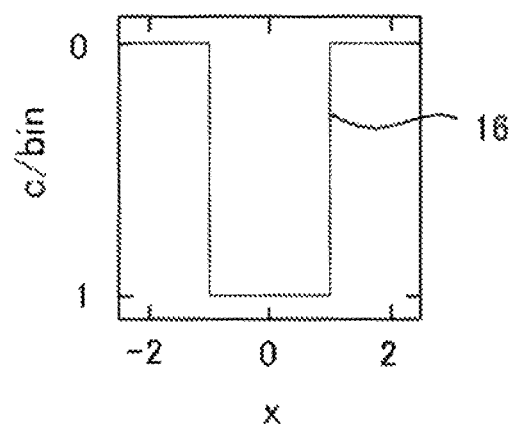
FIG. 9 is a diagram showing a particle-number distribution in a real-space direction in FIG. 8.
Figure 10:
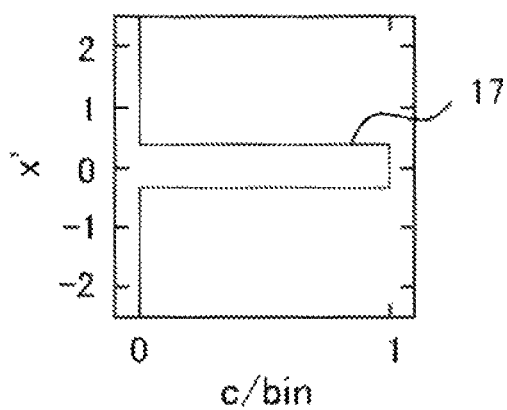
FIG. 10 is a diagram showing a particle-number distribution in an angular direction in FIG. 8.
Figure 11:
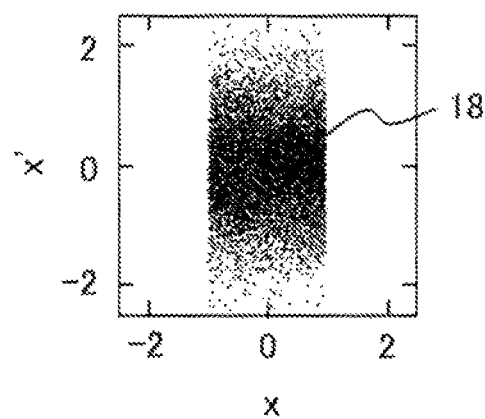
FIG. 11 is a diagram showing a normalized phase-space distribution in the x-direction of the beam having passed through the penumbra expander shown in FIG. 1.
Figure 12:
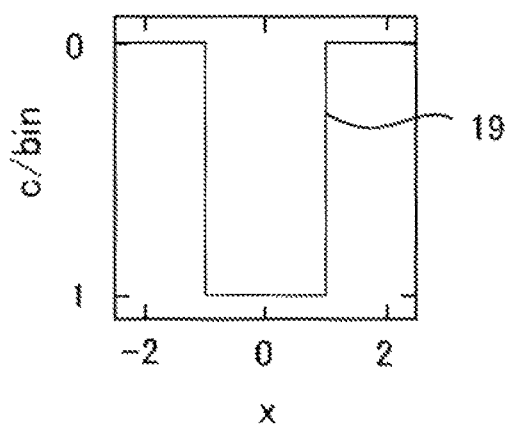
FIG. 12 is a diagram showing a particle-number distribution in a real-space direction in FIG. 11.
Figure 13:
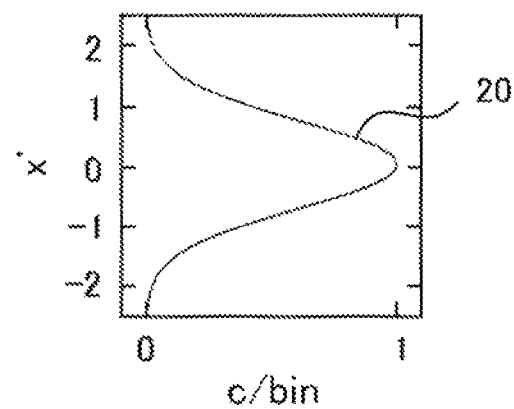
FIG. 13 is a diagram showing a particle-number distribution in an angular direction in FIG. 11.
Figure 14:
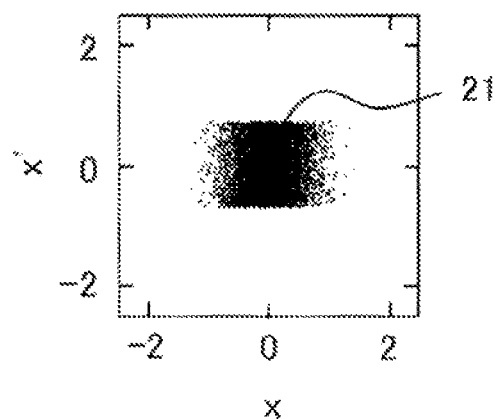
FIG. 14 is a diagram showing a normalized phase-space distribution in the x-direction at an isocenter shown in FIG. 1.
Figure 15:
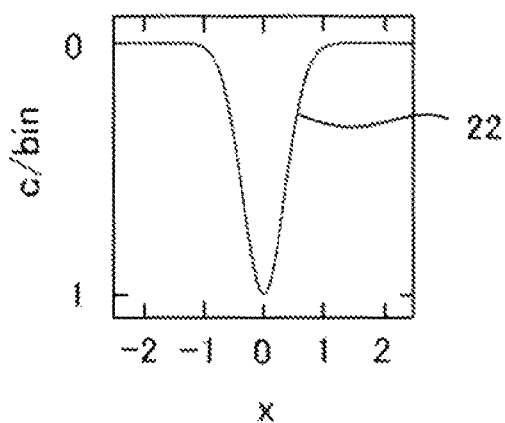
FIG. 15 is a diagram showing a particle-number distribution in a real-space direction in FIG. 14.
Figure 16:
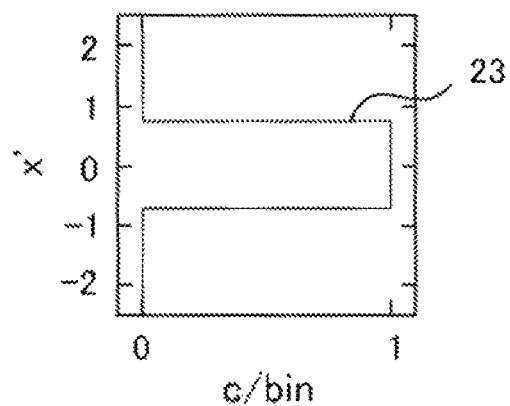
FIG. 16 is a diagram showing a particle-number distribution in an angular direction in FIG. 14.
Figure 17:
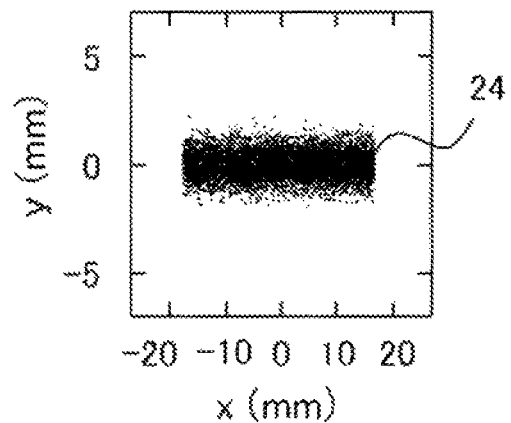
FIG. 17 is a diagram showing a real-space distribution of the beam to be inputted to the penumbra expander shown in FIG. 1.
Figure 18:
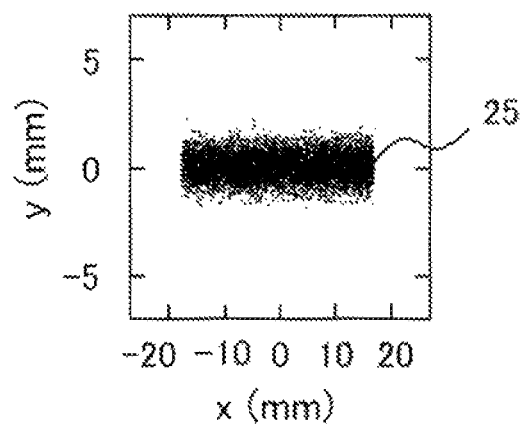
FIG. 18 is a diagram showing a real-space distribution of the beam having passed through the penumbra expander shown in FIG. 1.
Figure 19:
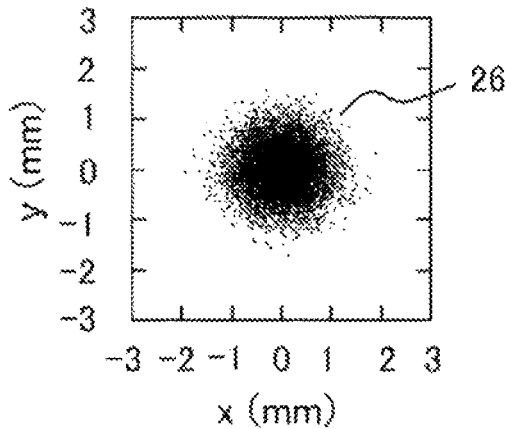
FIG. 19 is a diagram showing a real-space distribution of the beam at the isocenter shown in FIG. 1.

Next, examples of phase-space distribution and real-space distribution of the beam according to the beam shaping device 10 shown in FIG. 1, will be described. The distribution examples to be shown hereinafter are distribution examples at the inlet and outlet sides of the scatterer 6 as the penumbra expander 1 and at the isocenter. Because the beam profile is shaped only in the x-direction by the beam shaping device 10, only the phase-space distribution of the beam in the x-direction will be shown. FIG. 8 shows a normalized phase-space distribution in the x-direction of the beam to be inputted to the penumbra expander shown in FIG. 1. FIG. 9 is a diagram showing a particle-number distribution in the real-space direction in FIG. 8, and FIG. 10 is a diagram showing a particle-number distribution in the angular direction in FIG. 8. FIG. 11 is a diagram showing a normalized phase-space distribution in the x-direction of the beam having passed through the penumbra expander shown in FIG. 1. FIG. 12 is a diagram showing a particle-number distribution in the real-space direction in FIG. 11, and FIG. 13 is a diagram showing a particle-number distribution in the angular direction in FIG. 11. FIG. 14 is a diagram showing a normalized phase-space distribution in the x-direction at the isocenter shown in FIG. 1. FIG. 15 is a diagram showing a particle-number distribution in the real-space direction in FIG. 14, and FIG. 16 is a diagram showing a particle-number distribution in the angular direction in FIG. 14. FIG. 17 is a diagram showing a real-space distribution of the beam to be inputted to the penumbra expander shown in FIG. 1, and FIG. 18 is a diagram showing a real-space distribution of the beam having passed through the penumbra expander shown in FIG. 1. FIG. 19 is a diagram showing a real-space distribution of the beam at the isocenter shown in FIG. 1. In FIG. 8 to FIG. 19, such cases are shown where the beam size in the x-direction becomes nearly equal to the beam size in the y-direction, at the isocenter IC.

First, description will be made about the beam size, using FIG. 17 to FIG. 19. In FIG. 17 to FIG. 19, the abscissa represents a length (mm) in the x-direction and the ordinate represents a length (mm) in the y-direction. As shown in a real-space distribution 24 in FIG. 17, at the inlet side of the scatterer 6, the particle distribution in the x-direction is longer than the particle distribution in the y-direction. In the particle distribution in the x-direction, at its ends, the particle-number variation is steep. In the particle distribution in the y-direction, at its ends, white and black portions are gathered together, so that the particle-number variation is moderate. As shown in a real-space distribution 25 in FIG. 18, at the outlet side of the scatterer 6, the particle distribution in the x-direction and the particle distribution in the y-direction are both nearly unchanged from the distributions in FIG. 17. Because the betatron phase of the phase distribution in the x-direction is advanced, by an odd multiple of 90 degrees as described previously, as shown in a real-space distribution 26 in FIG. 19, at the isocenter IC, the particle-number variation is moderate in the particle distribution, in the x-direction. In addition, as shown in a real-space distribution 26 in FIG. 19, at the isocenter IC, the particle-number variation is also moderate in the particle distribution in the y-direction. Note that these real-space distributions of the beam are each a particle distribution in the beam cross-sectional direction.

In FIG. 8, FIG. 11 and FIG. 14, the abscissa represents a normalized real-space component x and the ordinate represents a normalized angle component x'. In FIG. 9, FIG. 12 and FIG. 15, the abscissa represents a normalized real-space component x and the ordinate represents a normalized particle number (c/bin). "bin" represents a bin width, which is 0.04 mm, here. In FIG. 10, FIG. 13 and FIG. 16, the abscissa represents a normalized particle number (c/bin) and the ordinate represents a normalized angle component x'. At the inlet side of the scatterer 6, the distribution of the angle components x' in the direction in which the end profile of the dose distribution in one-shot of the charged particle beam is desired to be moderated, is having been, narrowed by the pre-stage quadrupole electromagnet 3 so that its distribution width is as small as possible, as shown in the phase-space distribution 15 in FIG. 8. The distribution width, of the angle components x' is made extremely small, for example, at the position of the scatterer 6 by changing the parameters of the quadrupole electromagnets 2. As shown in a real-space directional characteristic 16 in FIG. 9, the particle number varies steeply at the ends with respect to the real-space component x in the phase-space distribution 15, and the particle number in the intermediate portion with respect to the real-space component x is constant. As shown in an angular directional characteristic 17 in FIG. 10, the particle number varies steeply at the ends with respect to the angle component x' in the phase-space distribution 15, and the particle number in the intermediate portion with respect to the angle component x' is constant.

At the outlet side of the scatterer 6, the distribution of the angle components x' in the direction in which the end profile of the dose distribution in one-shot of the charged particle beam is desired to be moderated, is having been expanded in the distribution width, by the scatterer 6, as shown in the phase-space distribution 18 in FIG. 11. In a real-space directional characteristic 19 in FIG. 12, like in the real-space directional characteristic 16 in FIG. 9, the particle number varies steeply at the ends with respect to the real-space component x in the phase-space distribution 18, and the particle number in the intermediate portion with respect to the real-space component x is constant. Because of the scatterer 6, in an angular directional characteristic 20 in FIG. 13, the particle number varies moderately from, the center (position indicated by x'=0) to the ends. As is shown from FIG. 12 and FIG. 13, the scatterer 6 causes only the particle-number distribution of the angle components x' in the phase-space distribution to vary moderately. In Embodiment 1, because the angle components x' in the phase-space distribution of the charged particle beam is having been sufficiently narrowed at the inlet side of the scatterer 6 as shown in FIG. 8, it is possible, at the outlet side of the scatterer 6, to eliminate, in the intermediate portion, a part where the particle number is constant, with respect to the angle component x' in the phase-space distribution of the charged particle beam, as shown in FIG. 13.

At the isocenter IC, the distribution of the real-space components x in the direction in which the end profile of the dose distribution in one-shot of the charged particle beam is desired to be moderated, is having been adjusted by the post-stage quadrupole electromagnet 4 so that the betatron phase becomes an odd multiple of 90 degrees as shown in a phase-space distribution 21 in FIG. 14. Thus, at its ends in the real-space direction, white and black portions are gathered together, so that the particle-number variation is moderate. Because of the post-stage quadrupole electromagnet 4, in a real-space directional characteristic 22 in FIG. 15, like in the distribution profile of the angular directional characteristic 20 in FIG. 13, the particle number varies moderately from the center (position indicated by x=0) to the ends. Because of the post-stage quadrupole electromagnet 4, in an angular directional characteristic 23 in FIG. 16, like in the distribution profile of the real-space directional characteristic 19 in FIG. 12, the particle number of the angle component x' varies steeply at the ends in the angular direction of the phase-space distribution 21, and the particle number of the angle component x' in the intermediate portion is constant.

As described above, the beam transport system 30 of Embodiment 1 is a beam transport system which includes the beam shaping device 10 by which the distribution profile of a charged particle beam having, at the end in the cross-sectional direction of the beam, a steep portion where the charged-particle number varies steeply, is shaped into a moderated form; and which transports the charged particle beam to the irradiation target that is positioned so as to include the isocenter IC as a positional reference for irradiation. Assuming that a direction perpendicular to the traveling direction (s-direction) of the charged particle beam and passing from the center of the charged particle beam to the steep portion is an x-direction, and inclinations of the charged particles forming the charged particle beam with respect to the traveling direction (s-direction), are angle components, the beam shaping device 10 in the beam transport system 30 in Embodiment 1 is characterized by including: the pre-stage quadrupole electromagnet 3 that reduces the distribution width of x-angle components x' that are the angle components x' in the x-direction of the charged particle beam; the penumbra expander 1 that moderates the end profile of the particle-number distribution of the x-angle components x' in the charged particle beam having passed through the pre-stage quadrupole electromagnet 3; and the post-stage quadrupole electromagnet 4 that adjusts the betatron phase in the phase-space distribution in the x-direction, of the charged particle beam having passed through the penumbra expander 1; wherein the post-stage quadrupole electromagnet 4 adjusts the betatron phase so that the phase advance angle thereof from the penumbra expander 1 to the isocenter IC is in a range of an odd multiple of 90 degrees±45 degrees. Namely, the beam shaping device 10 reduces the distribution width of the angle components in the x-direction of the charged particle beam to be inputted to the penumbra expander 1 and thereafter, moderates the end profile using the penumbra expander 1 and then adjusts the phase advance angle of the betatron phase toward the isocenter IC. Thus, it is possible to form an irradiation field having a distribution in which the particle number variation at the end is moderate, without undesirably increasing the beam size.

In addition, the beam shaping device 10 in Embodiment 1 has no restriction in its placement position in the beam transport system 30, and thus the beam shaping device 16 is highly flexible in the placement position. Thus, according to the beam transport system 30 of Embodiment 1, it is allowable to place the beam shaping device 10 on the upstream side away from the particle beam irradiation apparatus for irradiating the charged particle beam to the isocenter IC. According to the beam transport system 30 of Embodiment 1, unlike the system in Patent Document 1, it is possible to prevent an unwanted exposure due to neutrons produced from the scatterer 6, without increasing the device size of the beam shaping device 10, by placing the beam shaping device 10 on the upstream side away from the particle beam irradiation apparatus for irradiating the charged particle beam to the isocenter IC.

Embodiment 2

In Embodiment 1, with respect to the x-direction that is one of directions of the x-direction and the y-direction that are perpendicular to the beam traveling direction s, the breadth of the angle components x' in the phase-space distribution is optimized. In Embodiment 2, a case will be described in which the beam size in the y-direction is having been narrowed at the installation position of the scatterer 6 in order to make minimum a change in the particle distribution in the y-direction caused by the scatterer 6.

Figure 20:
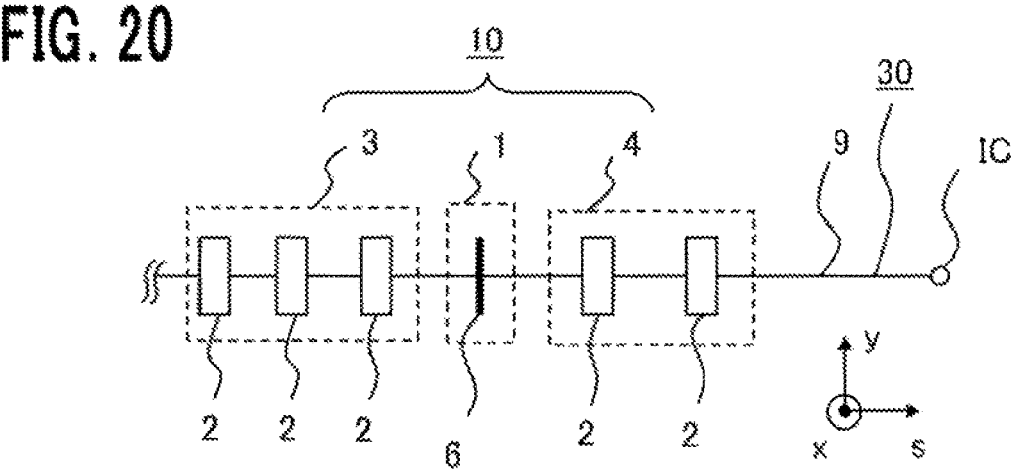
FIG. 20 is a diagram showing a beam transport system according to Embodiment 2 of the invention.

FIG. 20 is a diagram showing a beam transport system according to Embodiment 2 of the invention. The beam shaping device 10 in the beam transport system 30 of Embodiment 2 differs from the beam, shaping device 10 in the beam transport system 30 of FIG. 1 in that the pre-stage quadrupole electromagnet 3 includes three quadrupole electromagnets 2. Two of the quadrupole electromagnets 2 in the pre-stage quadrupole electromagnet 3 are provided, like in Embodiment 1, for narrowing the angle components x' in the phase-angle distribution so that they become as narrow as possible, and the other one of the quadrupole electromagnets 2 is provided for narrowing the real-space components y in the phase-space distribution so that they become as narrow as possible.

Figure 21:
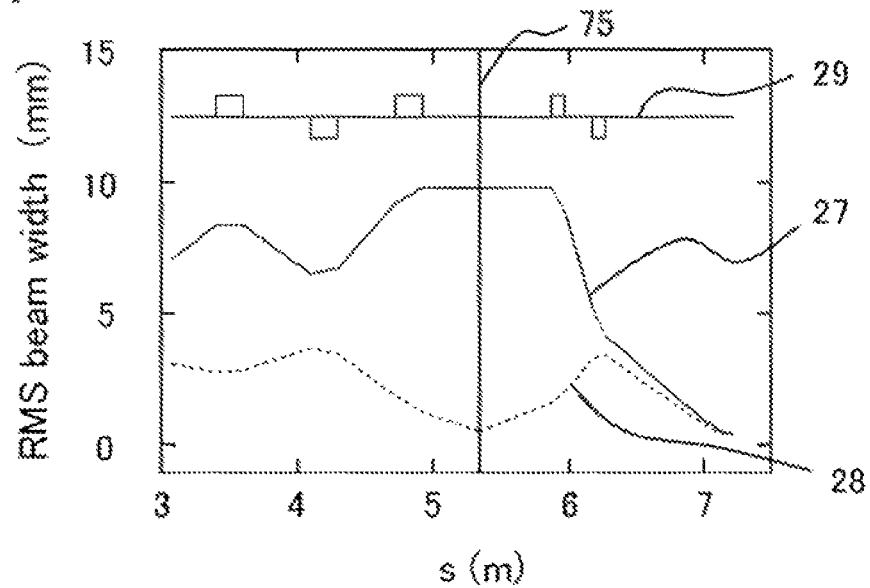
FIG. 21 is a diagram showing beam widths during beam transportation in the beam transport system of FIG. 20.

An example of beam-size variation is shown in FIG. 21. FIG. 21 is a diagram showing beam widths during beam transportation in the beam transport system of FIG. 20. The abscissa represents a length (m) in the beam traveling direction s, and the ordinate represents an RMS beam width (mm). RMS is root mean square. A beam size characteristic 27 is a variation characteristic of the beam size in the x-direction and a beam size characteristic 28 is a variation characteristic of the beam size in the y-direction. In FIG. 21, a quadrupole electromagnet placement 29 is also shown. Rectangles in the quadrupole electromagnet placement 29 indicate the placement positions of the respective quadrupole electromagnets 2, and the scatterer 6 is placed at the position indicated by a vertical line 75. The rectangles placed on the upper side of the quadrupole electromagnet placement 29 correspond to the quadrupole electromagnets for converging the beam, and the rectangles placed on the lower side correspond to the quadrupole electromagnets for diverging the beam. For example, the quadrupole electromagnet 2 for converging the beam that is placed at the left end of the pre-stage quadrupole electromagnet 3 is the quadrupole electromagnet for narrowing the real-space components y in the phase-space distribution so that they become as narrow as possible.

The example of beam-size variation shown in FIG. 21 is an example when an aluminum member having a thickness of 0.01 mm is used as the scatterer 6 for a proton beam of 250 MeV. Like in Embodiment 1, the direction in which the particle-number variation at the ends is desired to be moderated is x. According to the beam shaping device 10 in Embodiment 2, the beam size in the y-direction is having been narrowed at the position of the scatterer 6 (position indicated by the vertical line 75). This makes it possible for the beam shaping device 10 in Embodiment 2 to make minimum the change in the particle distribution (real directional-space components) in the y-direction, caused by the scatterer 6. The beam shaping device 10 in Embodiment 2 ensures flexibility for adjusting the beam size in the y-direction so that the size becomes small at the placement position of the scatterer 6, in such a manner that, in comparison with the beam shaping device 10 in Embodiment 1, one quadrupole electromagnet 2 is added to the pre-stage quadrupole electromagnet 3 placed upstream of the scatterer 6. In the beam shaping device 10 in Embodiment 1, if an aluminum member having a thickness of 0.01 mm is used as the scatterer 6 for a proton beam of 250 MeV and, like the arrangement in the quadrupole electromagnet placement 29, the quadrupole electromagnets 2 (other than the quadrupole electromagnet at the leftmost) are placed, the beam size characteristic in the x-direction of the beam transport system 30 of Embodiment 1 becomes the same as the beam size characteristic 27 in the x-direction in FIG. 21.

Figure 22:
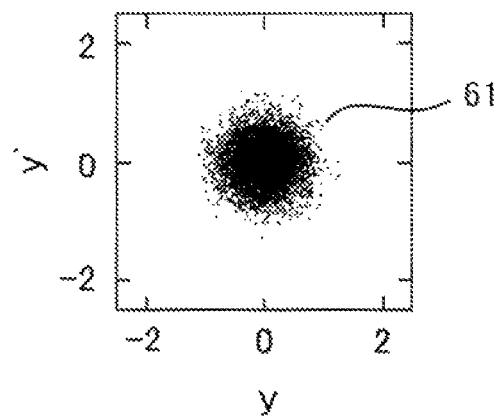
FIG. 22 is a diagram showing a normalized phase-space distribution in a y-direction of the beam to be inputted to a penumbra expander shown in FIG. 20.
Figure 23:
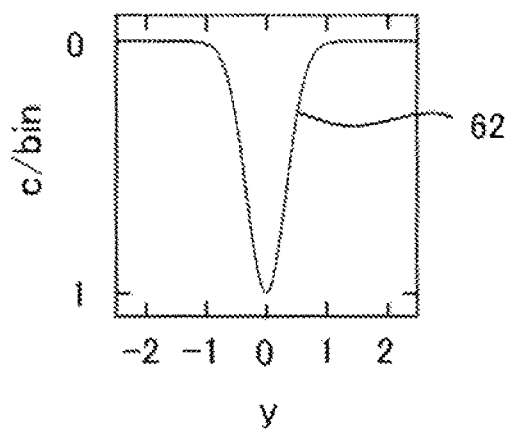
FIG. 23 is a diagram showing a particle-number distribution in a real-space direction in FIG. 22.
Figure 24:
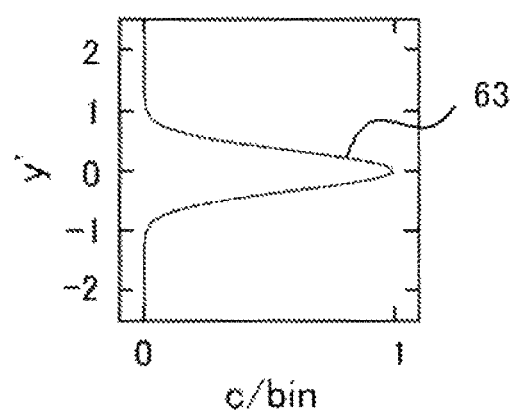
FIG. 24 is a diagram, showing a particle-number distribution in an angular direction in FIG. 22.
Figure 25:
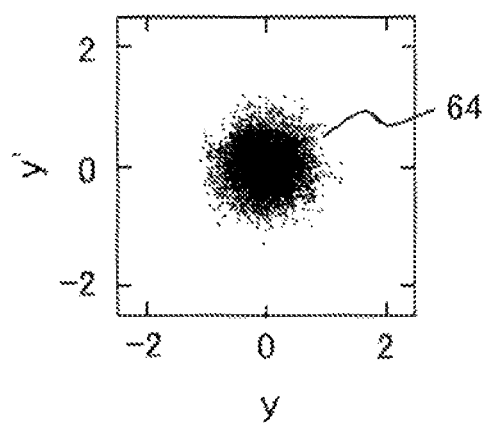
FIG. 25 is a diagram showing a normalized phase-space distribution in the y-direction of the beam having passed through the penumbra expander shown in FIG. 20.
Figure 26:
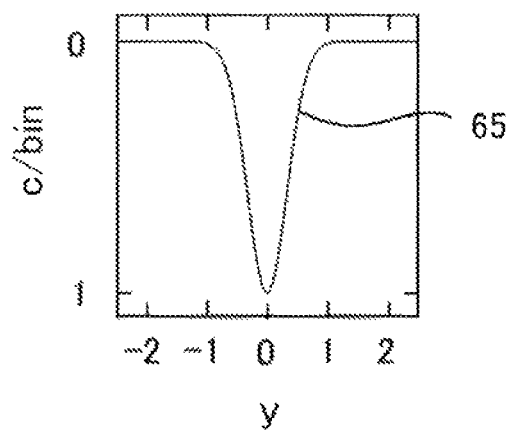
FIG. 26 is a diagram showing a particle-number distribution in a real-space direction in FIG. 25.
Figure 27:
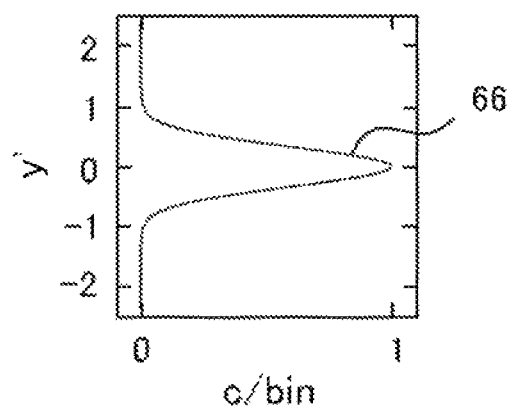
FIG. 27 is a diagram showing a particle-number distribution in an angular direction in FIG. 25.
Figure 28:
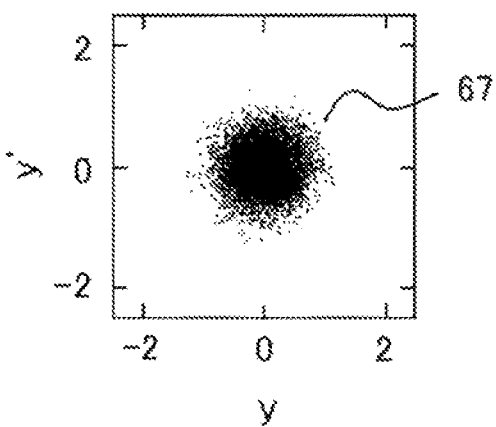
FIG. 28 is a diagram showing a normalized phase-space distribution in the y-direction at an isocenter shown in FIG. 20.
Figure 29:
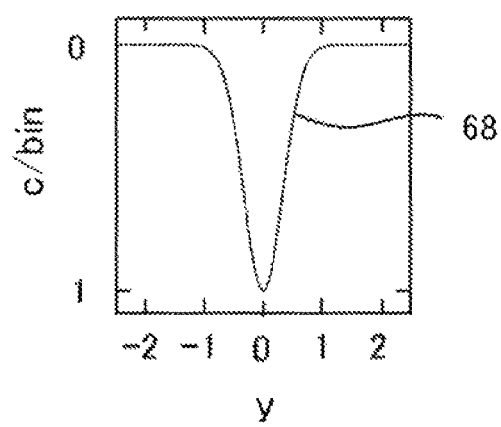
FIG. 29 is a diagram showing a particle-number distribution in a real-space direction in FIG. 28.
Figure 30:
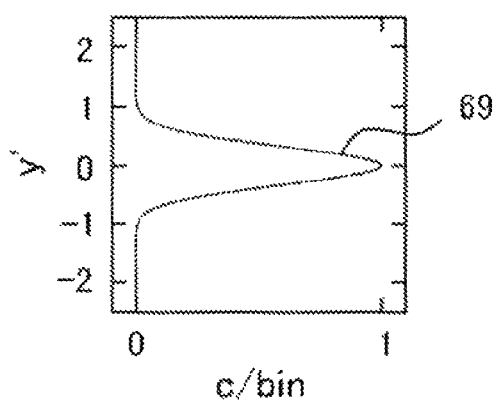
FIG. 30 is a diagram showing a particle-number distribution in an angular direction in FIG. 28.

Next, examples of phase-space distribution of the beam according to the beam shaping device 10 shown in FIG. 20, will be described. The distribution examples to be shown hereinafter are distribution examples at the inlet and outlet sides of the scatterer 6 as the penumbra expander 1 and at the isocenter. The phase-space distribution in the x-direction is similar to those in FIG. 8 to FIG. 16 illustrated in Embodiment 1, so that its description will not be repeated. The phase-space distribution in the y-direction is shown in FIG. 22 to FIG. 30. FIG. 22 shows a normalized phase-space distribution in the y-direction of the beam to be inputted to the penumbra expander shown in FIG. 20. FIG. 23 is a diagram showing a particle-number distribution in the real-space direction in FIG. 22, and FIG. 24 is a diagram showing a particle-number distribution in the angular direction in FIG. 22. FIG. 25 is a diagram showing a normalized phase-space distribution in the y-direction of the beam having passed through the penumbra expander shown in FIG. 20. FIG. 26 is a diagram showing a particle-number distribution in the real-space direction in FIG. 25, and FIG. 27 is a diagram showing a particle-number distribution in the angular direction in FIG. 25. FIG. 28 is a diagram showing a normalized phase-space distribution in the y-direction at the isocenter shown in FIG. 20. FIG. 29 is a diagram showing a particle-number distribution in the real-space direction in FIG. 28, and FIG. 30 is a diagram showing a particle-number distribution in the angular direction in FIG. 28.

In FIG. 22, FIG. 25 and FIG. 28, the abscissa represents a normalized real-space component y and the ordinate represents a normalized angle component y'. In FIG. 23, FIG. 26 and FIG. 29, the abscissa represents a normalized real-space component y and the ordinate represents a normalized particle number (c/bin). In FIG. 24, FIG. 27 and FIG. 30, the abscissa represents a normalized particle number (c/bin) and the ordinate represents a normalized angle component y'. At the inlet side of the scatterer 6, with respect to the real-space component y and the angle component y' in the phase-space distribution 61 in FIG. 22, white and black portions are gathered together at their ends, so that the particle-number variation is moderate. As shown in FIG. 23, in a real-space directional characteristic 62, the particle number varies moderately from the center (position indicated by y=0) to the ends. As shown in FIG. 24, in an angular directional characteristic 63, the particle number varies moderately from, the center (position indicated by y'=0) to the ends.

At the outlet side of the scatterer 6, with respect to the real-space component y and the angle component y' in the phase-space distribution 64 in FIG. 25, white and black portions are gathered together at their ends, so that the particle-number variation is moderate. As shown, in a real-space directional characteristic 65 in FIG. 26, the particle number varies moderately from the center (position indicated by y=0) to the ends. As shown in an angular directional characteristic 66 in FIG. 27, the particle number varies moderately from the center (position indicated by y'=0) to the ends. The phase-space distribution 64 at the outlet side of the scatterer 6 is nearly unchanged from the phase-space distribution 61 at the inlet side and thus, it is almost unaffected by the scatterer 6.

At the isocenter IC, with respect to the real-space component y and the angle component y' in a phase-space distribution 67 in FIG. 28, white and black portions are gathered together at their ends, so that the particle-number variation is moderate. As shown in FIG. 29, in a real-space directional characteristic 68, the particle number varies moderately from the center (position indicated by y=0) to the ends. As shown in FIG. 30, in an angular directional characteristic 69, the particle number varies moderately from the center (position indicated by y'=0) to the ends.

The beam, transport system 30 of Embodiment 2 includes, in the pre-stage electromagnet 3 of its beam shaping device 10, the quadrupole electromagnet 2 for narrowing the beam size in the y-direction, namely, the real-space components y in the phase-space distribution, at the installation position of the scatterer 6. Thus, it is possible to make smaller the change in the angle component y' in the y-direction caused by the scatterer 6 than that by the beam transport system 30 of Embodiment 1, so that, conclusively, the change in the real-space component y in the y-direction at the isocenter IC can be made smaller.

Embodiment 3

Figure 31:
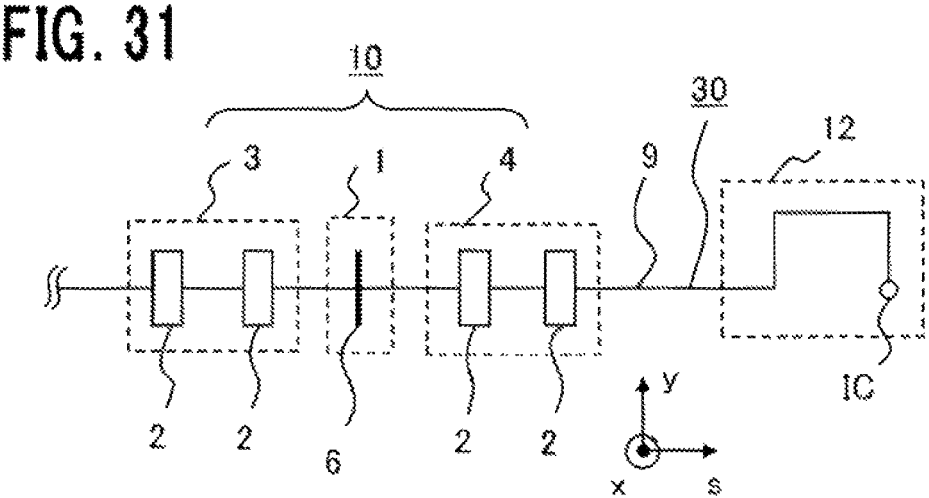
FIG. 31 is a diagram showing a beam transport system according to Embodiment 3 of the invention.

In Embodiment 3, a case will be described in which the downstream side in the beam transport system 30 is mounted on a rotary gantry 12. The rotary gantry 12 is configured so that it can rotate the particle beam irradiation apparatus for irradiating the charged particle beam, centering on the isocenter IC, to thereby irradiate the changed particle beam to the patient from an arbitrary rotation angle. FIG. 31 is a diagram showing the beam transport system according to Embodiment 3 of the invention. The isocenter IC is the point of intersection of the rotation axis of the rotary gantry 12 and the beam axis of the particle beam irradiation apparatus. In FIG. 31, although the beam shaping device 10 according to Embodiment 1 is illustrated as an example, it may be the beam shaping device 10 according to Embodiment 2. Note that, in FIG. 31, the beam passage 9 in the rotary gantry 12 is illustrated as it is bent at a right angle.

Because it is allowable to place the beam shaping device 10 of the invention on the upstream side in the beam transport system 30, the downstream side in the beam transport system 30 where the beam shaping device 10 is not placed, is allowed to be mounted on the rotary gantry 12. According to the beam transport system 30 of Embodiment 3, even when its downstream side is mounted on the rotary gantry 12, it is possible to transport the charged particle beam having a distribution in which the particle-number variation at its ends is moderate, without undesirably increasing the beam size by the beam shaping device 10.

Embodiment 4

Figure 32:
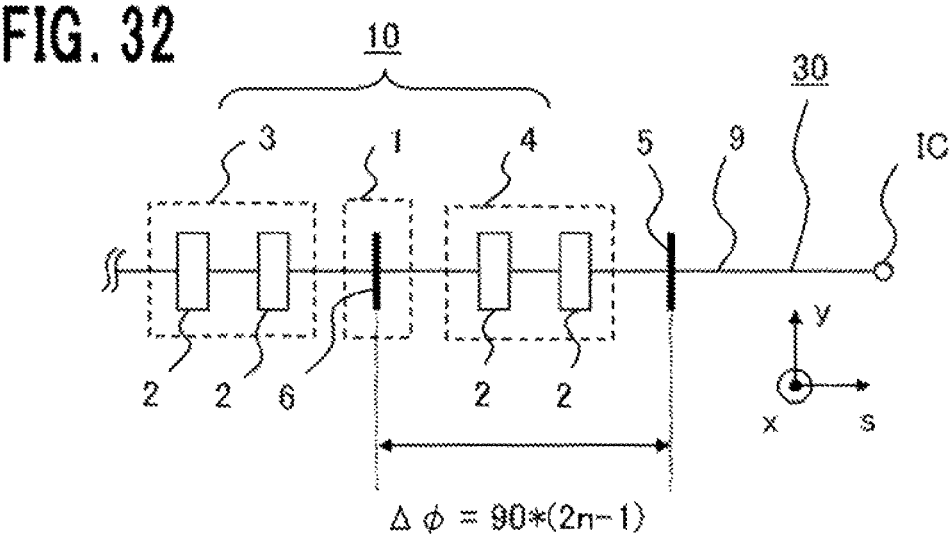
FIG. 32 is a diagram showing a beam transport system according to Embodiment 4 of the invention.

In Embodiment 4, a case will be described in which a beam-profile confirmation device 5, such as a screen monitor, a wire-grid monitor, or the like, is placed at the position where the advancement Δφ in the betatron phase from the scatterer 6 is an odd multiple of 90 degrees. In FIG. 32, Δφ is indicated by 90*(2n−1). The symbol "n" represents a natural number. According to the beam transport system 30 of Embodiment 4, because the beam-profile confirmation device 5 is used, it is possible to confirm whether a distribution in which the particle-number variation at the ends is moderate has been formed. According to the beam transport system 30 of Embodiment 4, because the beam profile can be confirmed using the beam-profile confirmation device 5, it is possible to easily adjust the beam shaping device 10, and to easily determine whether or not maintenance is necessary for the beam shaping device 10.

Embodiment 5

Figure 33:
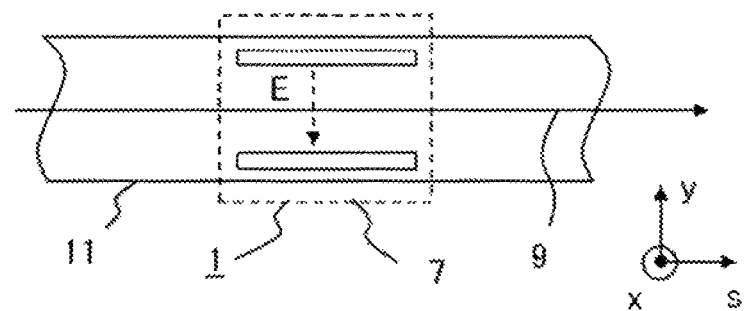
FIG. 33 is a diagram showing a penumbra expander according to Embodiment 5 of the invention.
Figure 34:
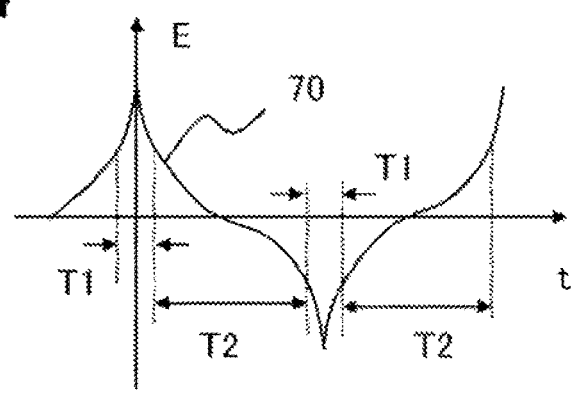
FIG. 34 is a diagram showing an electric-field distribution in the penumbra expander shown in FIG. 33.

In Embodiment 5, a case will be described in which, in place of the scatterer 6, a dipole electrode 7 or a dipole electromagnet 8 is applied as the penumbra expander 1. FIG. 33 is a diagram showing a penumbra expander according to Embodiment 5 of the invention, and FIG. 34 is a diagram showing an electric-field distribution in the penumbra expander in FIG. 33. The dipole electrode 7 is a parallel plate electrode, for example, and is placed inside a vacuum duct 11 of the beam transport system 30. In FIG. 34, the abscissa represents time t and the ordinate represents an electric field E. In an electric field characteristic 70, a period where the electric field E largely varies, namely, a period T1 where a kick angle is large, is made short, and a period T2 where the electric field E is weak, is made long. When such, a dipole electrode 7 is placed so that the electric field E is directed in the x-direction, it is possible to form the distribution in which the particle-number variation at the ends in the x-direction is moderate. As shown in FIG. 33, when the dipole electrode 7 is placed so that the electric field E is directed in the y-direction, it is possible to form the distribution in which the particle-number variation at the ends in the y-direction is moderate. The electric field E by the dipole electrode 7 is set to temporally vary much faster than the beam scanning speed for forming the irradiation field at the isocenter IC. Specifically, the electric field E is caused to vary at 1 MHz or more.

Figure 35:
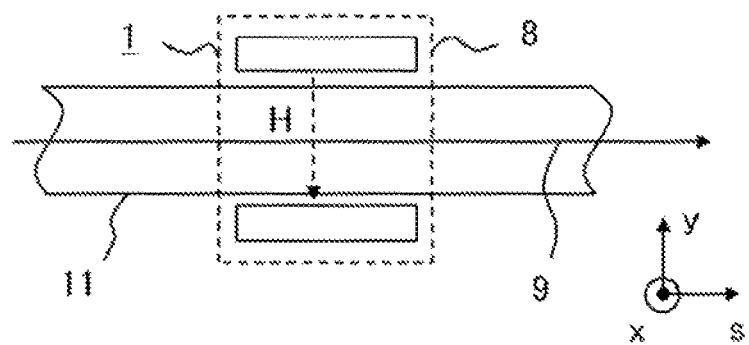
FIG. 35 is a diagram showing another penumbra expander according to Embodiment 5 of the invention.
Figure 36:
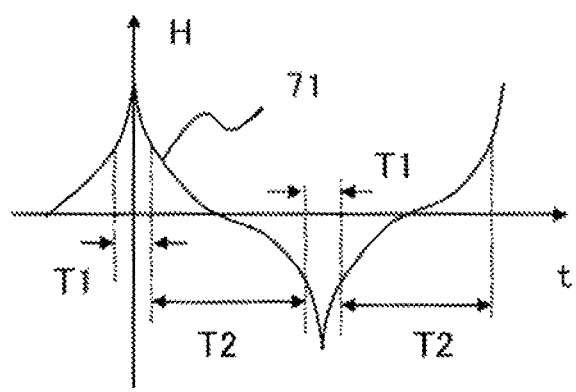
FIG. 36 is a diagram showing a magnetic-field distribution in the penumbra expander shown in FIG. 35.

FIG. 35 is a diagram showing another penumbra expander according to Embodiment 5 of the invention, and FIG. 36 is a diagram showing a magnetic-field distribution in the penumbra expander in FIG. 35. The dipole electromagnet 8 is placed outside the vacuum duct 11 of the beam transport system 30. In FIG. 36, the abscissa represents time t and the ordinate represents a magnetic field H. Like in the electric field characteristic 70, in a magnetic field characteristic 71, a period where the magnetic field H largely varies, namely, a period T1 where a kick angle is large, is made short, and a period T2 where the magnetic field H is weak, is made long. As shown in FIG. 35, when the dipole electromagnet 8 is placed so that the magnetic field H is directed in the y-direction, it is possible to form the distribution in which the particle-number variation at the ends in the x-direction is moderate. When, the dipole electromagnet 8 is placed so that the magnetic field H is directed in the x-direction, it is possible to form the distribution in which the particle-number variation at the ends in the y-direction is moderate. Like the electric field E by the dipole electrode 7, the magnetic field H by the dipole electromagnet 8 is set to temporally vary much faster than the beam scanning speed for forming the irradiation field at the isocenter IC. Specifically, the magnetic field H is caused to vary at 1 MHz or more.

When the penumbra expander 1 according to Embodiment 5 is applied to the beam shaping device 10, like in Embodiment 2, it is possible to form the distribution in which the particle-number variation is moderate at the ends only in a required direction. According to the beam transport system 30 of Embodiment 5, because the beam shaping device 10 includes the penumbra expander 1 that comprises the dipole electrode 7 or the dipole electromagnet 8, it is possible like in Embodiment 2, to make smaller the change in the real-space component y in the y-direction. than that by the scatterer 6 in the beam, transport system 30 of Embodiment 1.

Embodiment 6

In Embodiment 6, a particle beam therapy system will be described in which a synchrotron that utilizes a beam extraction method using betatron resonance (slow extraction method) is used as the accelerator of the beam generation apparatus, and in which the beam shaping device 10 described in Embodiment 1 to Embodiment 5 is placed in the beam transport system 30, downstream from the emission device of the synchrotron.

Figure 37:
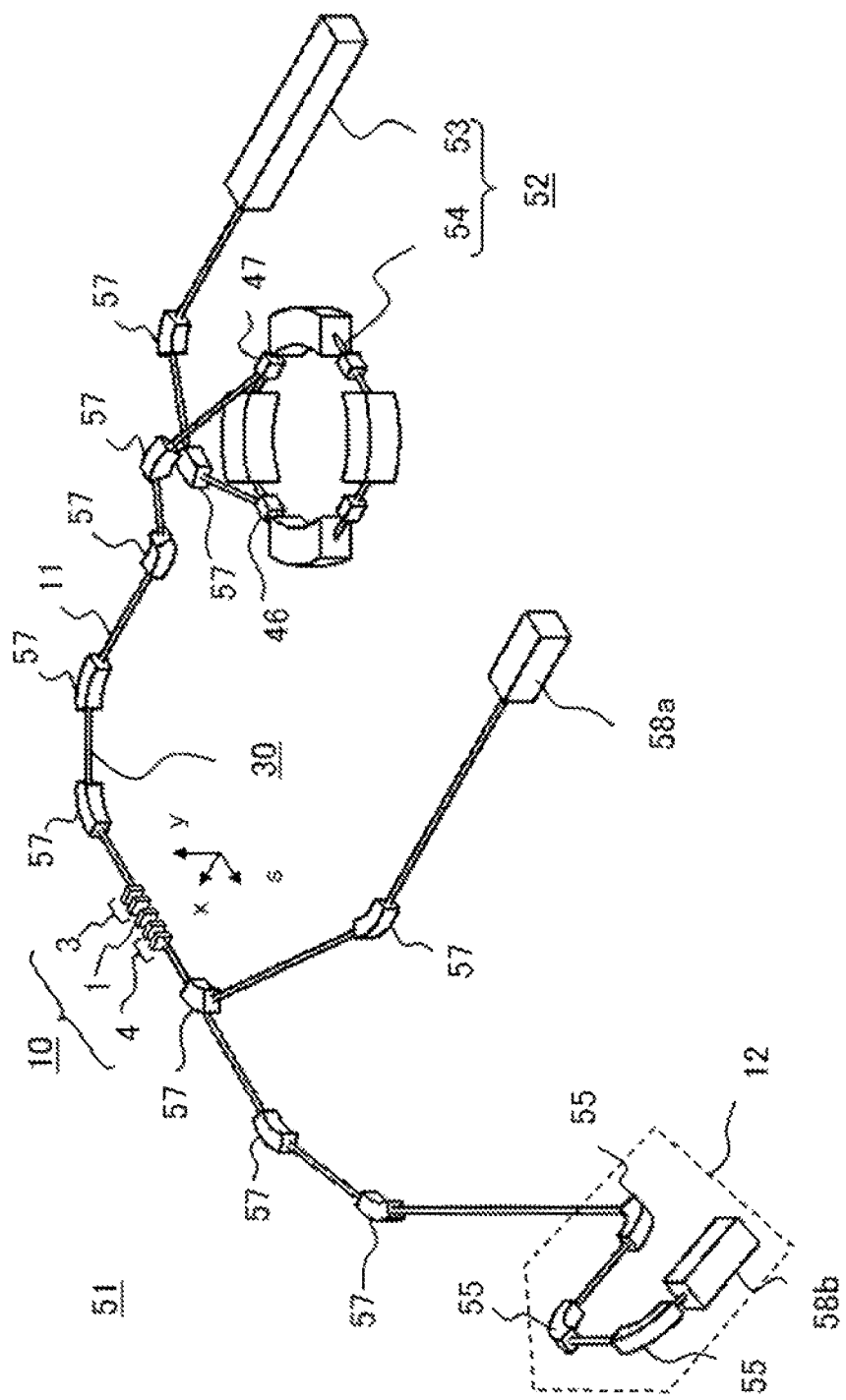
FIG. 37 is a schematic configuration diagram of a particle beam therapy system according to Embodiment 6 of the invention.
Figure 38:
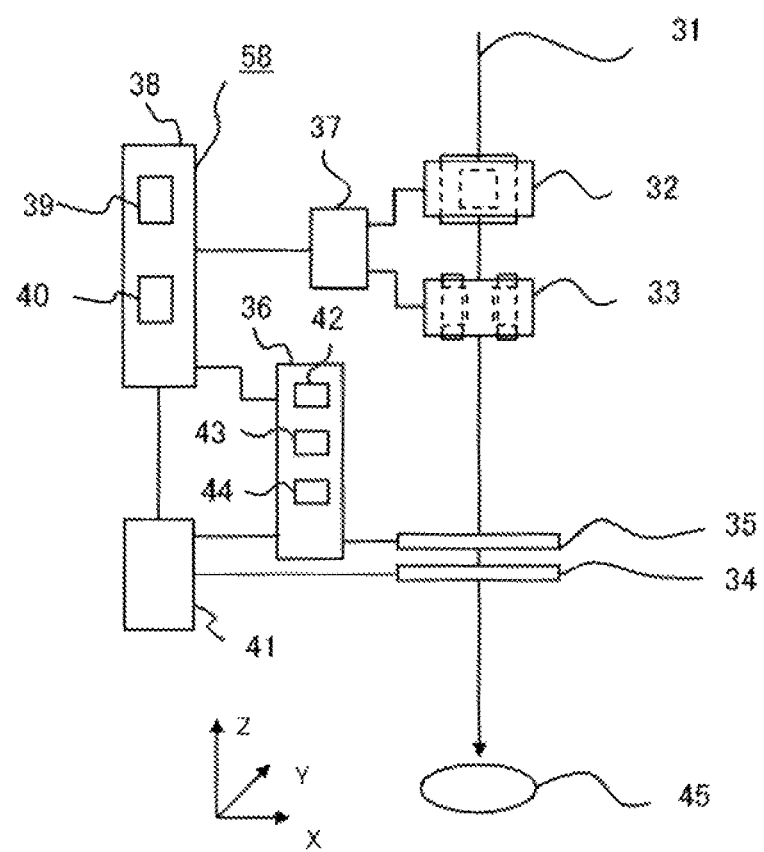
FIG. 38 is a diagram showing a configuration of a particle beam irradiation apparatus shown in FIG. 37.

FIG. 37 is a schematic configuration diagram of a particle beam therapy system according to the invention, and FIG. 38 is a diagram showing a configuration of a particle beam irradiation apparatus according to the invention. A particle beam therapy system 51 includes a beam generation apparatus 52, the beam transport system 30 and particle beam irradiation apparatuses 58a, 58b. The beam generation apparatus 52 includes an ion source (not shown), a pre-stage accelerator 53 and a synchrotron 54 as an accelerator. The particle beam irradiation apparatus 58b is placed in the rotary gantry 12. The particle beam irradiation apparatus 58a is placed in a treatment room having no rotary gantry 12.

The role of the beam transport system 30 is to communicate between the synchrotron 54 and the particle beam irradiation apparatuses 58a, 58b. The beam transport system 30 includes: the vacuum duct 11 through which the charged particle beam passes; a plurality of deflection electromagnets 57 for deflecting the charged particle beam; the beam shaping device 10; a plurality of deflection electromagnets 55 that is a part of the beam transport system 30 and is placed in the rotary gantry 12; and a plurality of unshown quadrupole electromagnets. The quadrupole electromagnets cause the charged particle beam to converge or diverge.

The charged particle beam that is a particle beam, such as a proton beam, etc., generated by the ion source, is accelerated by the pre-stage accelerator 53 and injected into the synchrotron 54 through an injection device 46. The charged particle beam is accelerated up to a given energy. The charged particle beam emitted from an emission device 47 of the synchrotron 54, is transported through the beam transport system 30 to the particle beam irradiation apparatuses 58a, 58b. The particle beam irradiation apparatuses 58a, 58b each irradiate the charged particle beam to an irradiation target 45 (see, FIG. 38). For the particle beam irradiation apparatuses, numeral 58 is used collectively, and numerals 58a, 58b are used when they are to be described distinctively.

A charged particle beam 31 generated and accelerated up to the given energy by the beam generation apparatus 52 is brought through the beam transport system 30 to the particle beam irradiation apparatus 58. In FIG. 38, the particle beam irradiation apparatus 58 includes: an X-direction scanning electromagnet 32 and a Y-direction scanning electromagnet 33 which scan the charged particle beam 31, respectively in an X-direction and a Y-direction that are directions perpendicular to the charged particle beam 31; a position monitor 34; a dose monitor 35; a dose-data converter 36; a beam-data processing device 41; a scanning-electromagnet power source 37; and an irradiation management device 38 for controlling the particle beam irradiation apparatus 58. The irradiation management device 38 includes an irradiation control computer 39 and an irradiation control device 40. The dose-data converter 36 includes a trigger generation unit 42, a spot counter 43 and an inter-spot counter 44. Note that the travelling direction of the charged particle beam 31 is a direction of −Z.

The X-direction scanning electromagnet 32 is a scanning electromagnet for scanning the charged particle beam 31 in the X-direction, and the Y-direction scanning electromagnet 33 is a scanning electromagnet for scanning the charged particle beam 31 in the Y-direction. With respect to the charged particle beam 31 scanned by the X-direction scanning electromagnet 32 and the Y-direction scanning electromagnet 33, the position monitor 34 detects beam information for calculating a passing position (gravity center position) and a size of the beam that passes therethrough. The beam-data processing device 41 calculates the passing position (gravity center position) and the size of the charged particle beam 31 on the basis of the beam information that comprises a plurality of analog signals (information about the beam) detected by the position monitor 34. Further, the beam-data processing device 41 generates an abnormality detection signal indicative of a position abnormality and/or a size abnormality of the charged particle beam 31, and output the abnormality detection signal to the irradiation management device 38.

The dose monitor 35 detects the dose of the charged particle beam 31. The irradiation management device 38 controls the irradiation position of the charged particle beam 31 in the irradiation target 45 on the basis of treatment plan data prepared by an unshown treatment plan device, and moves the charged particle beam 31 to a next irradiation position when the dose having been measured by the dose monitor 35 and converted by the dose-data converter 36 into digital data, reaches a target dose. The scanning-electromagnet power source 37 changes setup currents of the X-direction scanning electromagnet 32 and the X-direction scanning electromagnet 33 on the basis of control inputs (commands) outputted from the irradiation management device 38 for the X-direction scanning electromagnet 32 and the Y-direction scanning electromagnet 33.

Here, the scanning irradiation method of the particle beam irradiation apparatus 58 is assumed to be a raster-scanning irradiation method in which the charged particle beam 31 is not stopped when the irradiation position of the charged particle beam 31 is changed, that is a method in which the beam irradiation position moves between spot positions successively like a spot-scanning irradiation method. The spot counter 43 serves to measure the irradiation dose during when the beam irradiation position of the charged particle beam 31 is staying. The inter-spot counter 44 serves to measure the irradiation dose during when the beam irradiation position of the charged particle beam 31 is moving. The trigger generation unit 42 serves to generate a dose completion signal when the dose of the charged particle beam 31 at a beam irradiation position reaches the target irradiation dose.

The particle beam therapy system 51 of Embodiment 6 includes: the beam generation apparatus 52 that generates the charged particle beam 31 and accelerates it up to a given energy using the synchrotron 54; the beam transport system 30 that transports the charged particle beam 31 accelerated by the beam generation apparatus 52; and the particle beam irradiation apparatus 58 that irradiates the charged particle beam 31 transported by the beam transport system 30 to the irradiation target 45; wherein the beam transport system 30 includes the beam shaping device 10. The beam shaping device 10 is that described in Embodiments 1 to 5. According to the particle beam therapy system 51 of Embodiment 6, because the beam shaping device 10 is provided in the beam transport system 30, it is possible to irradiate to the irradiation target, the charged particle beam having a distribution in which the particle-number variation at the ends is moderate, and to form for the irradiation target, the irradiation field having a distribution in which the particle-number variation at the ends is moderate, without undesirably increasing the beam size.

According to the particle beam therapy system 51 of Embodiment 6, the beam shaping device 10 is placed on the upstream side of one particle beam irradiation apparatuses 58a, 58b, so that, unlike the therapy system in Patent Document 1, even when the scatterer 6 is used as the penumbra expander 1, it is possible to prevent an unwanted exposure due to neutrons produced from the scatterer 6, without increasing the device size of the beam shaping device 10. Further, as shown in FIG. 37, the beam shaping device 10 is allowed to be placed on the upstream side of the deflection electromagnet 57 at which the passage is branched coward the plural particle beam irradiation apparatuses 58a, 58b. In this manner, according to the particle beam therapy system 51 of Embodiment 6, it suffices to place only one beam shaping device 10. Thus, it is possible to transport the charged particle beam having a distribution in which the particle-number variation at the ends is moderate, to the plural particle beam irradiation apparatuses 58, without enlarging and complexing the system, as well as without undesirably increasing the beam size. Note that, in FIG. 37, such a case is illustrated in which the post-stage quadrupole electromagnet 4 of the beam shaping device 10 is placed between the penumbra expander 1 and the deflection electromagnet 57 that is nearest to and on the downstream side of the penumbra expander 1; however, the post-stage quadrupole electromagnet 4 may be placed in a distributed manner between the deflection electromagnet 57 that is nearest to and on the downstream side of the penumbra expander 1, and the particle beam irradiation apparatus 58a. Likewise, in the case of beam transportation to the particle beam irradiation apparatus 58b, the post-stage quadrupole electromagnet 4 of the beam shaping device 10 may be placed in a distributed manner between the deflection electromagnet 57 that is nearest to and on the downstream side of the penumbra expander 1, and the particle beam irradiation apparatus 58b.

Embodiment 7

In Embodiment 7, a particle beam therapy system will be described in which a cyclotron is used as the accelerator of the beam generation apparatus 52, and in which a scatterer as an energy modifier, a collimator for limiting the beam size, and the beam shaping device 10 described in Embodiment 1 to Embodiment 5, are placed in the beam transport system 30.

Figure 39:
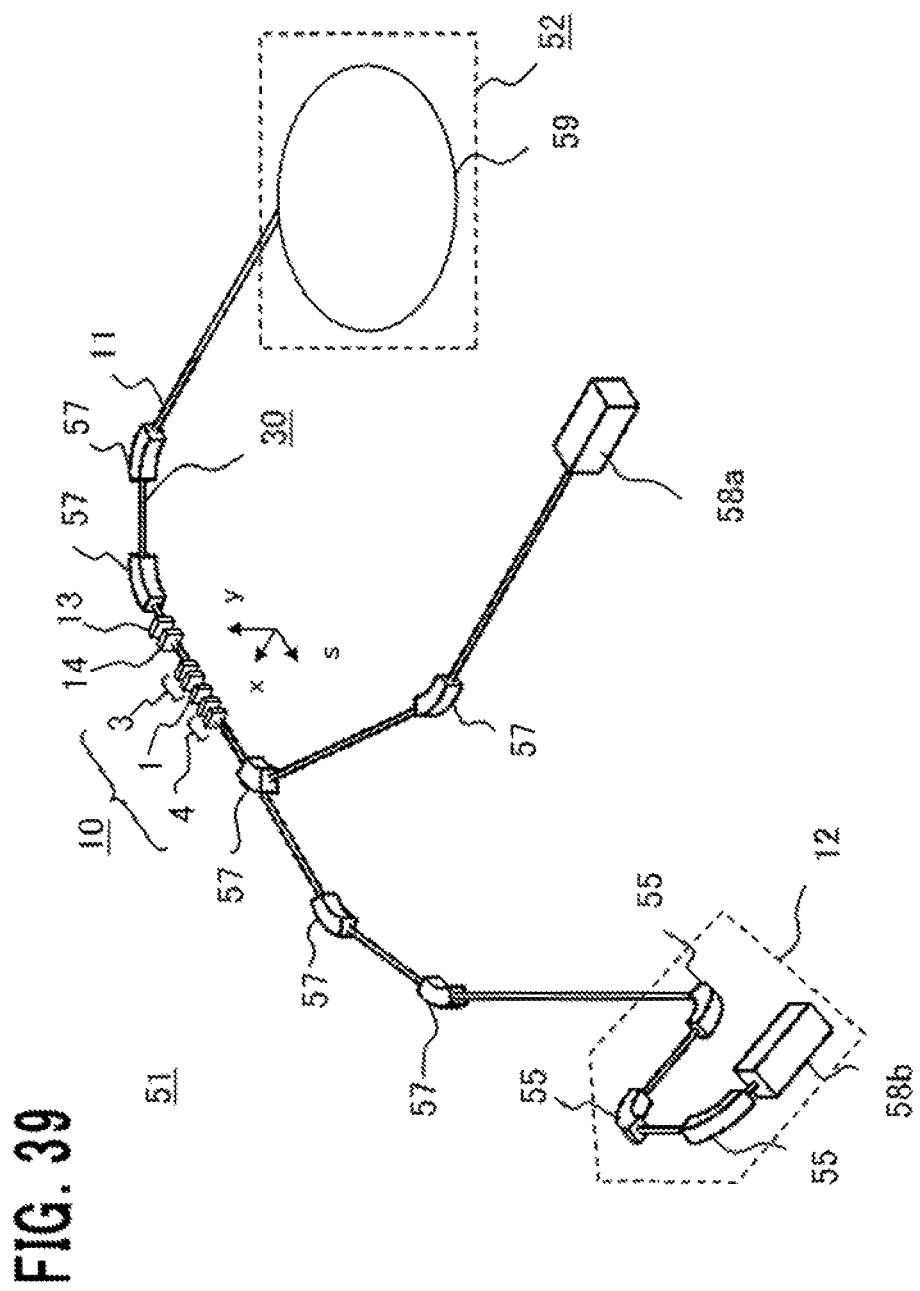
FIG. 39 is a schematic configuration diagram of a particle beam therapy system according to Embodiment 7 of the invention.

FIG. 39 is a schematic configuration diagram of the particle beam therapy system according to Embodiment 7 of the invention. The particle beam therapy system 51 of Embodiment 7 differs from the particle beam therapy system 51 of Embodiment 6 in that the accelerator of the beam generation apparatus 52 is a cyclotron 59, and a scatterer 13 and a collimator 14 are provided between the cyclotron 59 and the beam shaping device 10. The collimator 14 is placed on the downstream side of the scatterer 13 and limits the beam size expanded by the scatterer. The beam shaping device 10 shapes the distribution profile at the ends having been cut to become steep by the collimator 14. The penumbra expander 1 is placed at the position at which the advancement in the betatron phase from the collimator 14 is 90 degrees. This makes it possible for the penumbra expander 1 to moderate the particle-number variation at the ends with respect to the angle components x' in the phase-space distribution.

According to the particle beam therapy system 51 of Embodiment 7, an effect similar to that by the particle beam therapy system 51 of Embodiment 6 is achieved.

Note that, in Embodiments 6, 7, the description has been made with an irradiation method in which the charged particle beam 31 is stopped at the time the slide is changed, and the charged particle beam 31 is kept irradiated at the time the portions in the same slice are irradiated; however, the irradiation method is not limited thereto, and the invention may also be applied to another irradiation method of spot scanning in which the charged particle beam 31 is stopped for every irradiation spot, or raster scanning, or the like. Further, any combination of the respective embodiments, and any appropriate modification or omission in the embodiments may be made in the present invention without departing from the scope of the invention.

DESCRIPTION OF REFERENCE NUMERALS AND SIGNS

1: penumbra expander, 3: pre-stage quadrupole electromagnet, 4: post-stage quadrupole electromagnet, 5: beam-profile confirmation device, 6: scatterer, 7: dipole electrode, 8: dipole electromagnet, 10: beam shaping device, 12: rotary gantry, 13: scatterer, 14: collimator, 30: beam transport system, 31: charged particle beam, 45: irradiation target, 51: particle beam therapy system, 52: beam generation apparatus, 54: synchrotron, 58, 58a, 58b: particle beam irradiation apparatus, 59: cyclotron, IC: isocenter.

The invention claimed is:

1. A beam transport system which comprises a beam shaping device by which a distribution profile of a charged particle beam having, at an end in a cross-sectional direction of the beam, a steep portion where a particle number varies steeply, is shaped into a moderated form; and which transports the charged particle beam to an irradiation target that is positioned so as to include an isocenter as a positional reference for irradiation;
   wherein, assuming that a direction perpendicular to a traveling direction of the charged particle beam and passing from a center of the charged particle beam to the steep portion is an x-direction, and inclinations of charged particles forming the charged particle beam with respect to the traveling direction, are angle components, the beam shaping device comprises:
   a pre-stage quadrupole electromagnet that reduces a distribution width of x-angle components that are the angle components in the x-direction in the charged particle beam;
   a penumbra expander that moderates an end profile of a particle-number distribution of the x-angle components in the charged particle beam having passed through the pre-stage quadrupole electromagnet; and
   a post-stage quadrupole electromagnet that adjusts a betatron phase in a phase-space distribution in the x-direction, of the charged particle beam having passed through the penumbra expander; and
   wherein the post-stage quadrupole electromagnet adjusts the betatron phase so that a phase advance angle thereof from the penumbra expander to the isocenter is in a range of an odd multiple of 90 degrees±45 degrees.

2. The beam transport system of claim 1, wherein the pre-stage quadrupole electromagnet comprises:
   at least two quadrupole electromagnets for reducing the distribution width of the x-angle components in the charged particle beam; and
   a quadrupole electromagnet for reducing a beam size in a y-direction that is perpendicular to the traveling direction of the charged particle beam and perpendicular to the x-direction.

3. The beam transport system of claim 1, further comprising a beam-profile confirmation device for confirming a beam profile, at a position where the phase advance angle of the betatron phase from the penumbra expander is an odd multiple of 90 degrees.

4. The beam transport system of claim 1, wherein the penumbra expander is a scatterer with a thickness of 0.1 mm or less.

5. The beam transport system of claim 1, wherein the penumbra expander comprises a dipole electrode;
   wherein the dipole electrode generates a periodically-varying electric field; and
   wherein, in the electric field, a period that is large in variation is shorter than a period that is small in variation, and their frequency is 1 MHz or more.

6. The beam transport system of claim 1, wherein the penumbra expander comprises a dipole electromagnet;
   wherein the dipole electromagnet generates a periodically-varying magnetic field; and wherein, in the magnetic field, a period that is large in variation is shorter than a period that is small in variation, and their frequency is 1 MHz or more.

7. A particle beam therapy system comprising: a beam generation apparatus that generates a charged particle beam and accelerates it up to a given energy using a synchrotron; a beam transport system that transports the charged particle beam accelerated by the beam generation apparatus; and a particle beam irradiation apparatus that irradiates the charged particle beam transported by the beam transport system to an irradiation target;
    wherein said beam transport system is the beam transport system in claim 1.

8. A particle beam therapy system comprising: a beam generation apparatus that generates a charged particle beam and accelerates it up to a given energy using a cyclotron; a beam transport system that transports the charged particle beam accelerated by the beam generation apparatus; and a particle beam irradiation apparatus that irradiates the charged particle beam transported by the beam transport system to an irradiation target;
    wherein said beam transport system is the beam transport system in claim 1, and includes a scatterer for changing energy of the charged particle beam and a collimator for limiting a beam size expanded by the scatterer, between the cyclotron and the beam shaping device; and
    wherein the penumbra expander of the beam shaping device is placed at a position where a phase advance angle of the betatron phase from the collimator is 90 degrees.

9. The particle beam therapy system of claim 7, further comprising a rotary gantry for rotating the particle beam irradiation apparatus centering on the isocenter;
    wherein the penumbra expander is placed on the upstream side of the rotary gantry.

10. The beam transport system of claim 2, further comprising a beam-profile confirmation device for confirming a beam profile, at a position where the phase advance angle of the betatron phase from the penumbra expander is an odd multiple of 90 degrees.

11. The beam transport system of claim 2, wherein the penumbra expander is a scatterer with a thickness of 0.1 mm or less.

12. The beam transport system of claim 3, wherein the penumbra expander is a scatterer with a thickness of 0.1 mm or less.

13. The beam transport system of claim 2, wherein the penumbra expander comprises a dipole electrode;
    wherein the dipole electrode generates a periodically-varying electric field; and
    wherein, in the electric field, a period that is large in variation is shorter than a period that is small in variation, and their frequency is 1 MHz or more.

14. The beam transport system of claim 3, wherein the penumbra expander comprises a dipole electrode;
    wherein the dipole electrode generates a periodically-varying electric field; and
    wherein, in the electric field, a period that is large in variation is shorter than a period that is small in variation, and their frequency is 1 MHz or more.

15. The beam transport system of claim 2, wherein the penumbra expander comprises a dipole electromagnet;
    wherein the dipole electromagnet generates a periodically-varying magnetic field; and
    wherein, in the magnetic field, a period that is large in variation is shorter than a period that is small in variation, and their frequency is 1 MHz or more.

16. The beam transport system of claim 3, wherein the penumbra expander comprises a dipole electromagnet;
    wherein the dipole electromagnet generates a periodically-varying magnetic field; and
    wherein, in the magnetic field, a period that is large in variation is shorter than a period that is small in variation, and their frequency is 1 MHz or more.

17. A particle beam therapy system comprising: a beam generation apparatus that generates a charged particle beam and accelerates it up to a given energy using a synchrotron; a beam transport system that transports the charged particle beam accelerated by the beam generation apparatus; and a particle beam irradiation apparatus that irradiates the charged particle beam transported by the beam transport system to an irradiation target;
    wherein said beam transport system is the beam transport system in claim 2.

18. A particle beam therapy system comprising: a beam generation apparatus that generates a charged particle beam and accelerates it up to a given energy using a synchrotron; a beam transport system that transports the charged particle beam accelerated by the beam generation apparatus; and a particle beam irradiation apparatus that irradiates the charged particle beam transported by the beam transport system to an irradiation target;
    wherein said beam transport system is the beam transport system in claim 3.

19. A particle beam therapy system comprising: a beam generation apparatus that generates a charged particle beam and accelerates it up to a given energy using a cyclotron; a beam transport system that transports the charged particle beam accelerated by the beam generation apparatus; and a particle beam irradiation apparatus that irradiates the charged particle beam transported by the beam transport system to an irradiation target;
    wherein said beam transport system is the beam transport system in claim 2, and includes a scatterer for changing energy of the charged particle beam and a collimator for limiting a beam size expanded by the scatterer, between the cyclotron and the beam shaping device; and
    wherein the penumbra expander of the beam shaping device is placed at a position where a phase advance angle of the betatron phase from the collimator is 90 degrees.

20. The particle beam therapy system of claim 8, further comprising a rotary gantry for rotating the particle beam irradiation apparatus centering on the isocenter;
    wherein the penumbra expander is placed on the upstream side of the rotary gantry.

\* \* \* \* \*